: (12) United States Patent
Hakeem et al.

(10) Patent No.: US 10,386,345 B2
(45) Date of Patent: Aug. 20, 2019

(54) METHOD AND SYSTEM FOR AN OXYGEN SENSOR

(71) Applicant: Ford Global Technologies, LLC, Dearborn, MI (US)

(72) Inventors: Mohannad Hakeem, Dearborn, MI (US); James Eric Anderson, Dearborn, MI (US); Shuya Shark Yamada, Novi, MI (US); Gopichandra Surnilla, West Bloomfield, MI (US)

(73) Assignee: Ford Global Technologies, LLC, Dearborn, MI (US)

(*) Notice: Subject to any disclaimer, the term of this patent is extended or adjusted under 35 U.S.C. 154(b) by 472 days.

(21) Appl. No.: 14/663,243

(22) Filed: Mar. 19, 2015

(65) Prior Publication Data
US 2016/0274073 A1 Sep. 22, 2016

(51) Int. Cl.
G01N 30/72 (2006.01)
G01N 33/28 (2006.01)
G01N 30/88 (2006.01)

(52) U.S. Cl.
CPC ..... *G01N 30/7206* (2013.01); *G01N 33/2829* (2013.01); *G01N 2030/8854* (2013.01)

(58) Field of Classification Search
CPC .................................................. G01N 30/7206
USPC ........................................................ 702/24
See application file for complete search history.

(56) References Cited

U.S. PATENT DOCUMENTS

| 6,170,318 B1* | 1/2001 | Lewis ................. G01N 27/126 340/632 |
| 6,739,177 B2 | 5/2004 | Sato et al. |
| 2004/0149591 A1* | 8/2004 | Klein ........................ B01J 4/00 205/628 |
| 2006/0125826 A1* | 6/2006 | Lubkowitz ......... G01N 30/8675 345/440 |
| 2006/0232267 A1* | 10/2006 | Halalay .............. G01N 33/2888 73/53.05 |
| 2007/0151846 A1* | 7/2007 | Klein ........................ C01B 3/00 204/237 |
| 2013/0213012 A1* | 8/2013 | Van Nieuwstadt ... F02D 41/029 60/274 |
| 2014/0120626 A1* | 5/2014 | Stubbs .................... C10L 1/003 436/56 |
| 2015/0075502 A1 | 3/2015 | Surnilla et al. |

(Continued)

OTHER PUBLICATIONS

Hakeem, M. et al. "Characterization and Speciation of Fuel Oil Dilution in Gasoline Direct Injection (DI) Engines," ICEF No. ICEF2015-1072, ASME 2015 Internal Combustion Engine Division Fall Technical Conference ICEF 2015, Nov. 8-11, 2015, 8 pages.

(Continued)

*Primary Examiner* — Moazzam Hossain
*Assistant Examiner* — Omar F Mojaddedi
(74) *Attorney, Agent, or Firm* — Julia Voutyras; McCoy Russell LLP

(57) ABSTRACT

Examples are provided for estimating an amount of fuel in an engine oil and an effect of the fuel on a gas sensor. In one example, an apparatus may include an analyzer to analyze an engine fluid and a computing device operably coupled to the analyzer, the computing device storing non-transitory instructions executable to determine fuel dilution in engine oil based on speciation of hydrocarbons in fuel in the engine oil determined based on output received from the analyzer.

19 Claims, 8 Drawing Sheets

(56) References Cited

U.S. PATENT DOCUMENTS

| | | | |
|---|---|---|---|
| 2015/0121864 A1 | 5/2015 | Surnilla et al. | |
| 2016/0177716 A1* | 6/2016 | Zuo | G01V 8/10 702/8 |
| 2016/0178602 A1* | 6/2016 | Gras | C10L 1/003 73/23.39 |

OTHER PUBLICATIONS

Hakeem, M. et al., "Methods and Systems for Determining a Fuel Concentration in Engine Oil Using an Intake Oxygen Sensor," U.S. Appl. No. 14/252,679, filed Apr. 14, 2014, 63 pages.

Surnilla, G. et al., "Methods and Systems for Adjusting EGR Based on an Impact of PCV Hyrdrocarbons on an Intake Oxygen Sensor," U.S. Appl. No. 14/252,693, filed Apr. 14, 2014, 63 pages.

Hakeem, M. et al., "Method for Reducing Engine Oil Dilution," U.S. Appl. No. 14/512,318, filed Oct. 10, 2014, 45 pages.

Hakeem, M. et al., "Method for Adjusting a Grille Shutter Opening," U.S. Appl. No. 14/591,789, filed Jan. 7, 2015, 77 pages.

Sagawa, T. et al., "Study of Fuel Dilution in Direct-Injection and Multipoint Injection Gasoline Engines," SAE Technical Paper Series No. 2002-01-1647, International Spring Fuels & Lubricants Meeting & Exhibition, Reno, Nevada, May 6-9, 2002, 11 pages.

Saji, K. "Characteristics of Limiting Current-Type Oxygen Sensor," Journal of the Electrochemical Society 134.10 (1987): 2430-2435,1987, 6 pages.

"Agilent 7890A Gas Chromatograph Operating Guide," Agilent Technologies, Inc., Jun. 2010, 84 pages.

Iyer, C. et al. "Oil Dilution Metrics Development for GTDI Engines," Ford Motor Company, Dec. 10, 2014, 10 pages.

Mackay, D. et al. "Correlation of Chemical Evaporation Rate with Vapor Pressure," Environ. Sci. Technol., 2014, 5 pages.

* cited by examiner

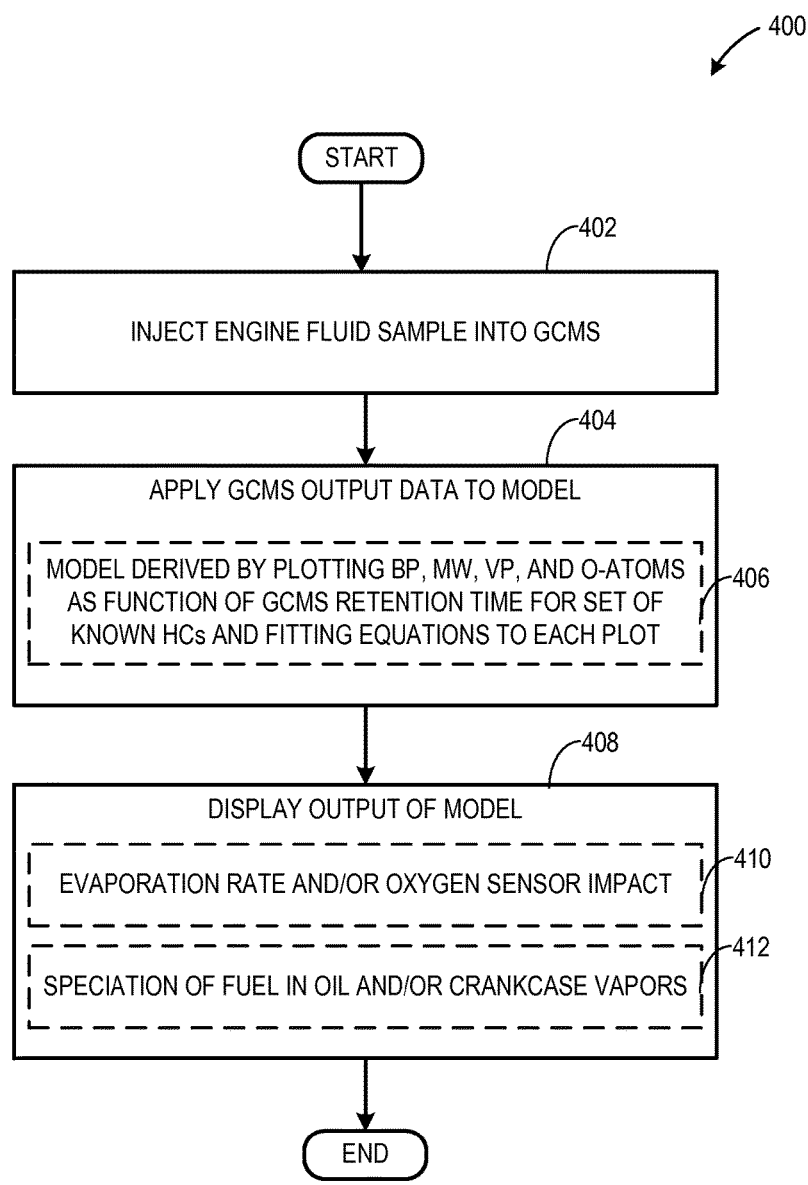

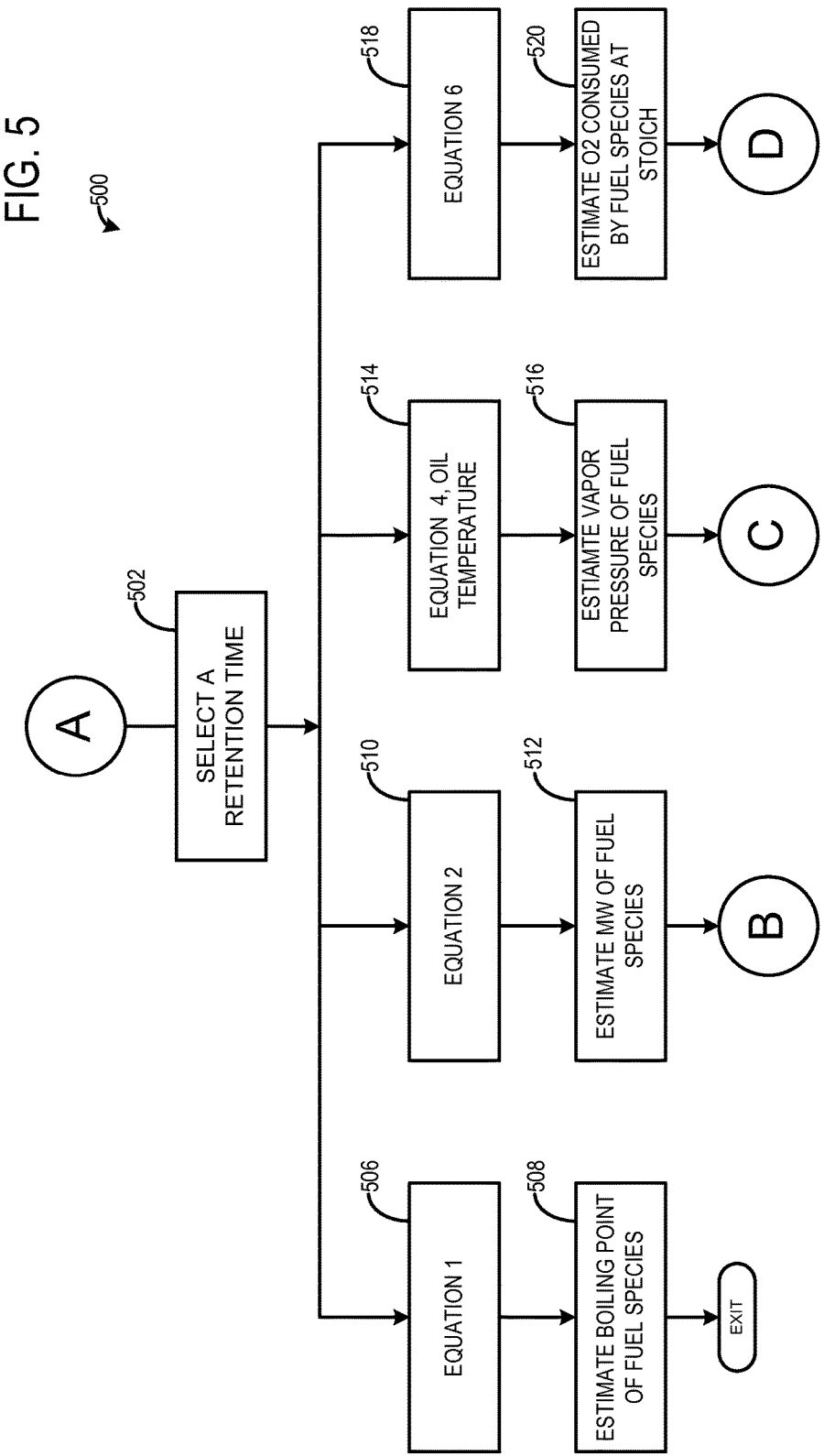

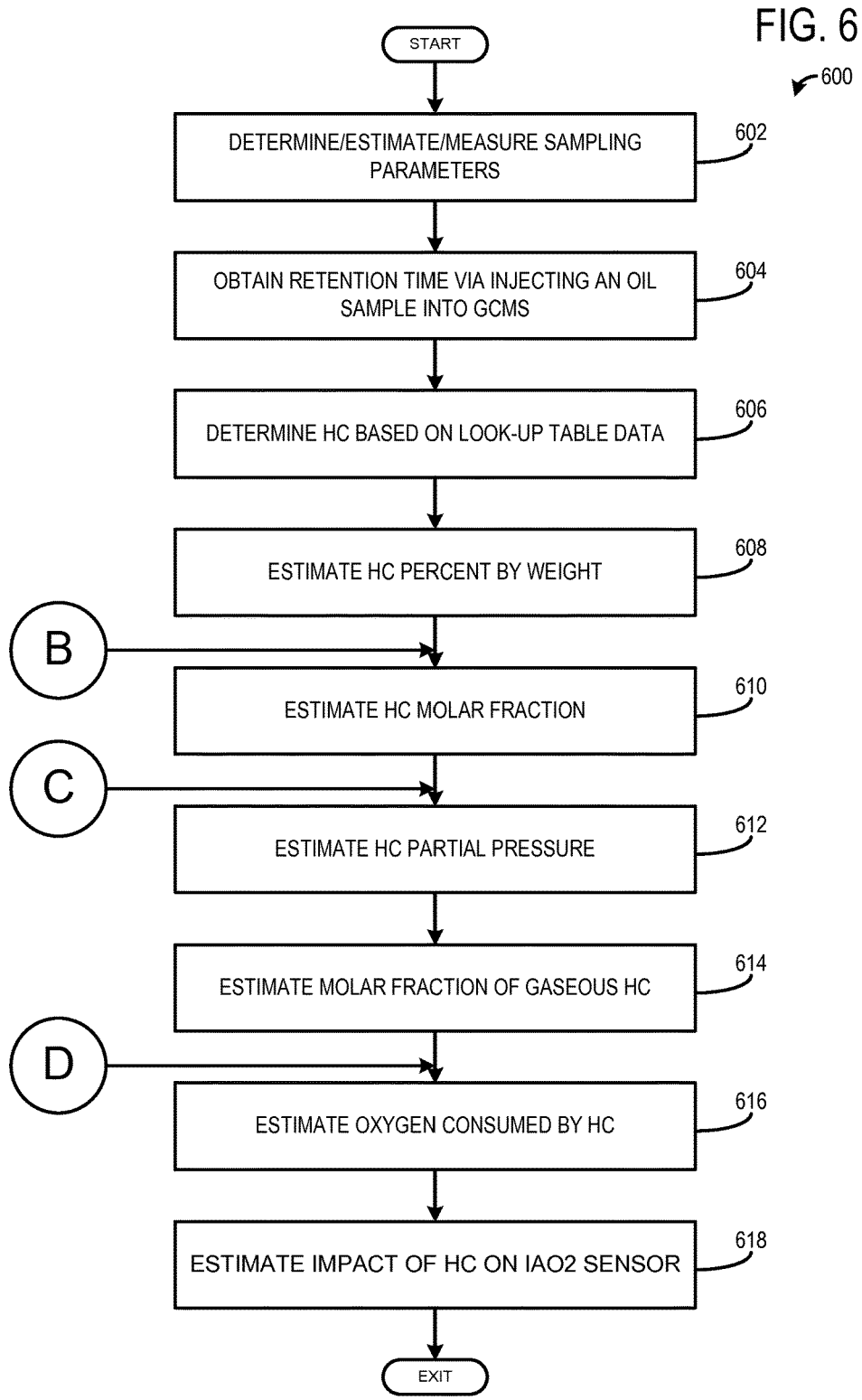

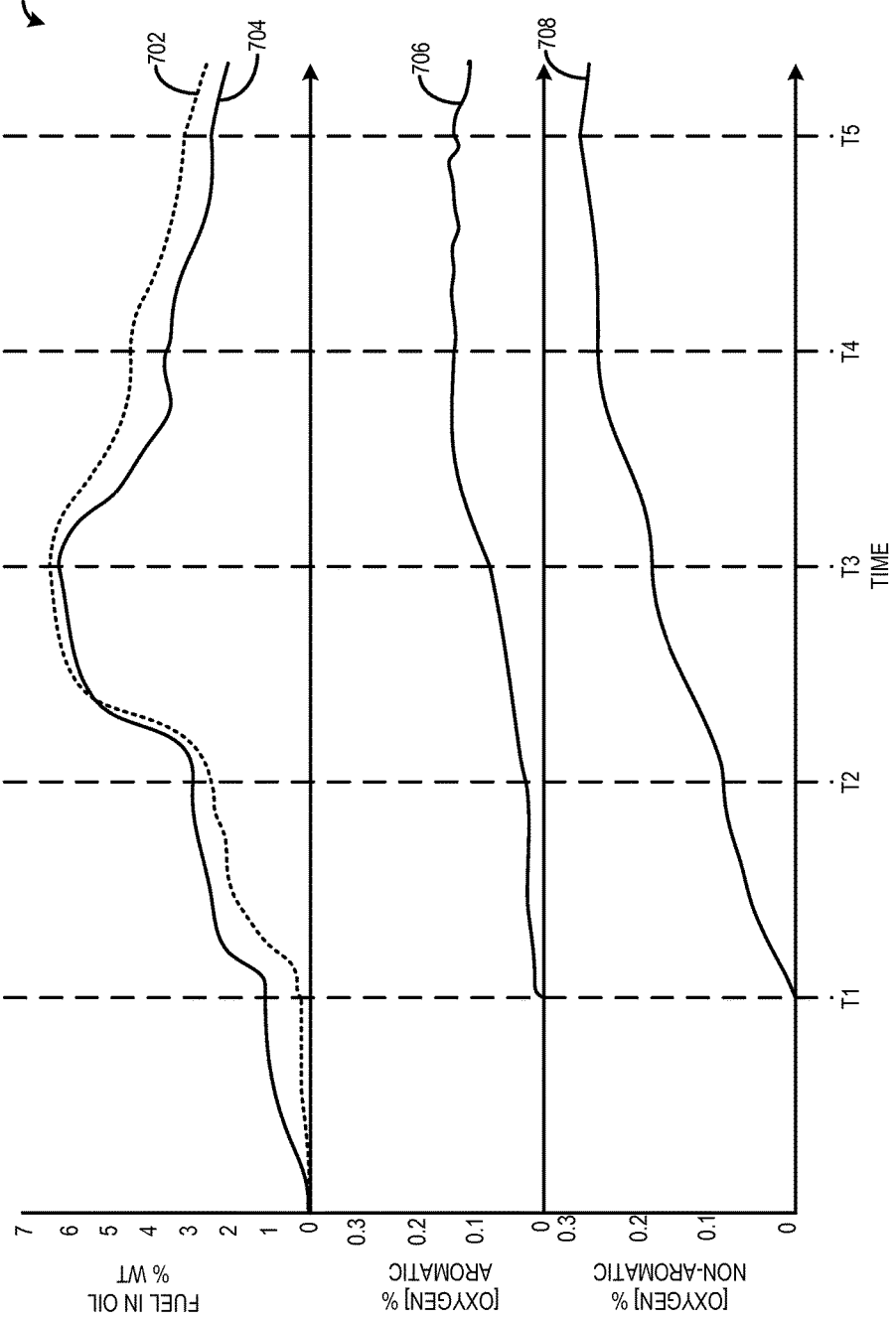

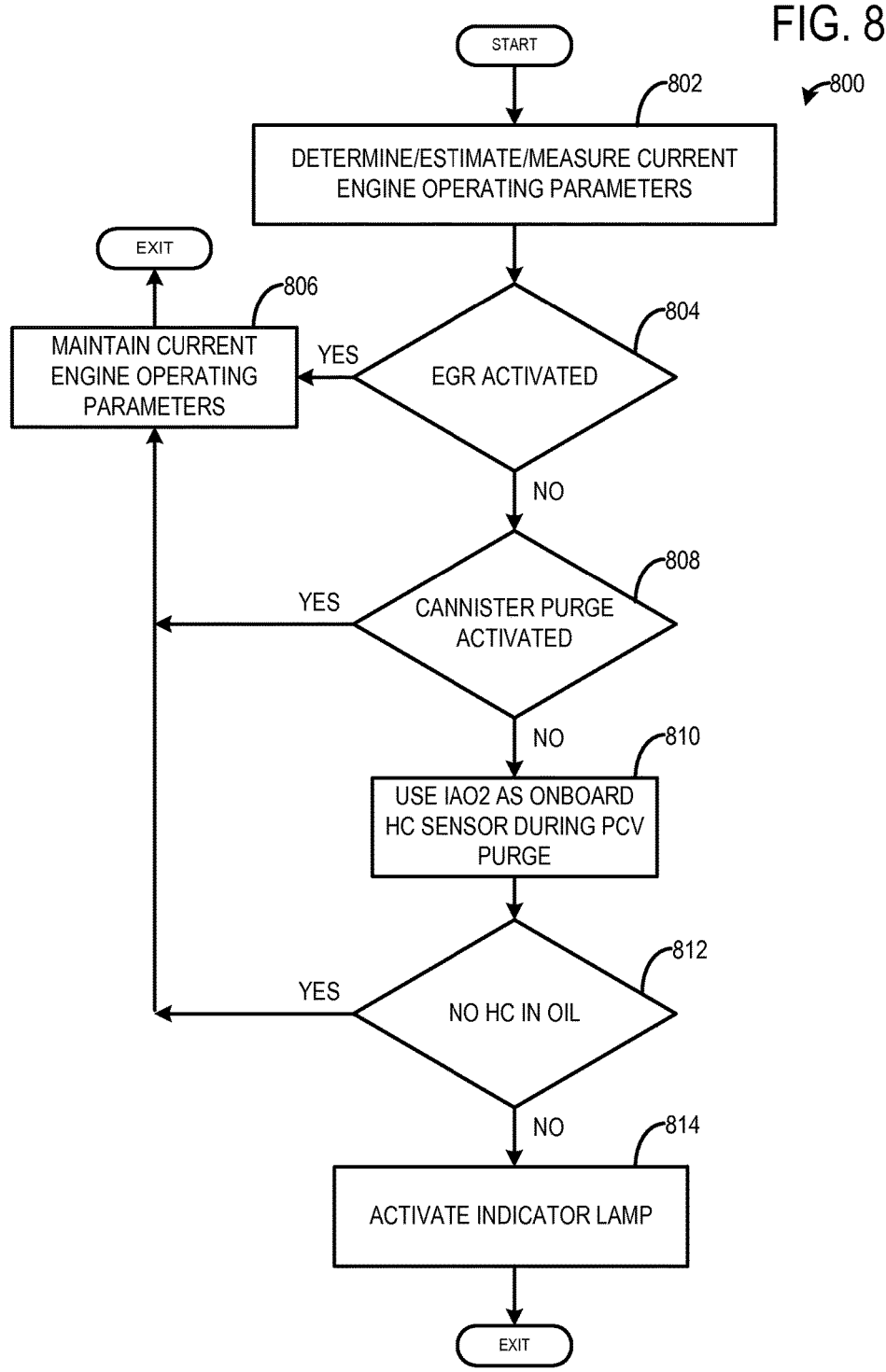

METHOD AND SYSTEM FOR AN OXYGEN SENSOR

FIELD

The present description relates generally to methods and systems for detecting hydrocarbon species present in an engine fluid.

BACKGROUND/SUMMARY

In certain engine configurations, particular direct injection engines, fuel may accumulate in engine oil in a crankcase of the engine, for example during engine cold start and warm-up conditions, by impinging along the cylinder bore walls and flowing to the crankcase oil sump. The accumulated fuel may then evaporate out of the oil and into the crankcase while the engine is warming up and when the engine oil reaches a steady-state operating temperature. The crankcase vapors may be passed to the engine during crankcase purge. Fuel present in the oil and/or crankcase may affect various engine parameters and controls including fuel control and monitoring, engine oil viscosity, and the intake oxygen sensor output. Excessive fuel in the oil may decrease engine durability.

Attempts to address the above identified issues have included adjusting engine operation based on a fuel concentration in engine oil. However, the inventors herein have recognized an issue with the above approach. Such approaches typically assume that the fuel present in the oil is of similar composition as the fuel injected to the engine. However, the hydrocarbon species that accumulate in the oil and that evaporate into the crankcase may differ from the injected fuel, and the inventors herein have further recognized that these various species may differentially impact intake oxygen sensor output, for example.

Accordingly, an apparatus is provided to identify various hydrocarbon species present in an engine fluid. In one example, an apparatus comprises an analyzer to analyze an engine fluid and a computing device operably coupled to the analyzer, the computing device storing non-transitory instructions executable to determine fuel dilution in engine oil based on speciation of hydrocarbons in fuel in the engine oil determined based on output received from the analyzer.

In one example, the analyzer may include a gas chromatographer mass spectrometer (GC-MS) configured to output information usable by the computing device to identify each hydrocarbon species, and the concentration of each species, present in sampled engine oil. For example, the GC-MS may output a GC retention time for each of a plurality of engine oil fractions. Based on the retention times, as well as GC-MS data for a known set of hydrocarbon species, the hydrocarbon species present in the engine oil may be determined. Further, by determining various engine operating parameters at the time of sampling, such as engine oil temperature and crankcase pressure, the identity of various hydrocarbon species that have evaporated out of the engine oil and into the crankcase may be estimated. Based on identity and concentration of the hydrocarbon species in the crankcase and engine oil, more accurate engine fuel control, oil quality monitoring, and other parameters may be provided. Further, by identifying the hydrocarbon species present in the crankcase, an effect of the hydrocarbons on an oxygen sensor, such as an intake oxygen sensor, may be determined.

It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

FIG. 4 depicts a method for analyzing an oil sample to determine a fuel-oil dilution.
FIG. 5 depicts a flow chart illustrating a method for calculating a variety of characteristics for a fuel species.
FIG. 6 depicts a flow chart illustrating a method for estimating a total fuel species effect based on a summation of individual fuel species effects.
FIG. 7 depicts a plot illustrating hydrocarbon accumulation in the engine oil and the hydrocarbons effect on the intake air oxygen sensor.
FIG. 8 depicts a flow chart for using an intake air oxygen sensor for determining fuel in oil.

DETAILED DESCRIPTION

Figure 1:
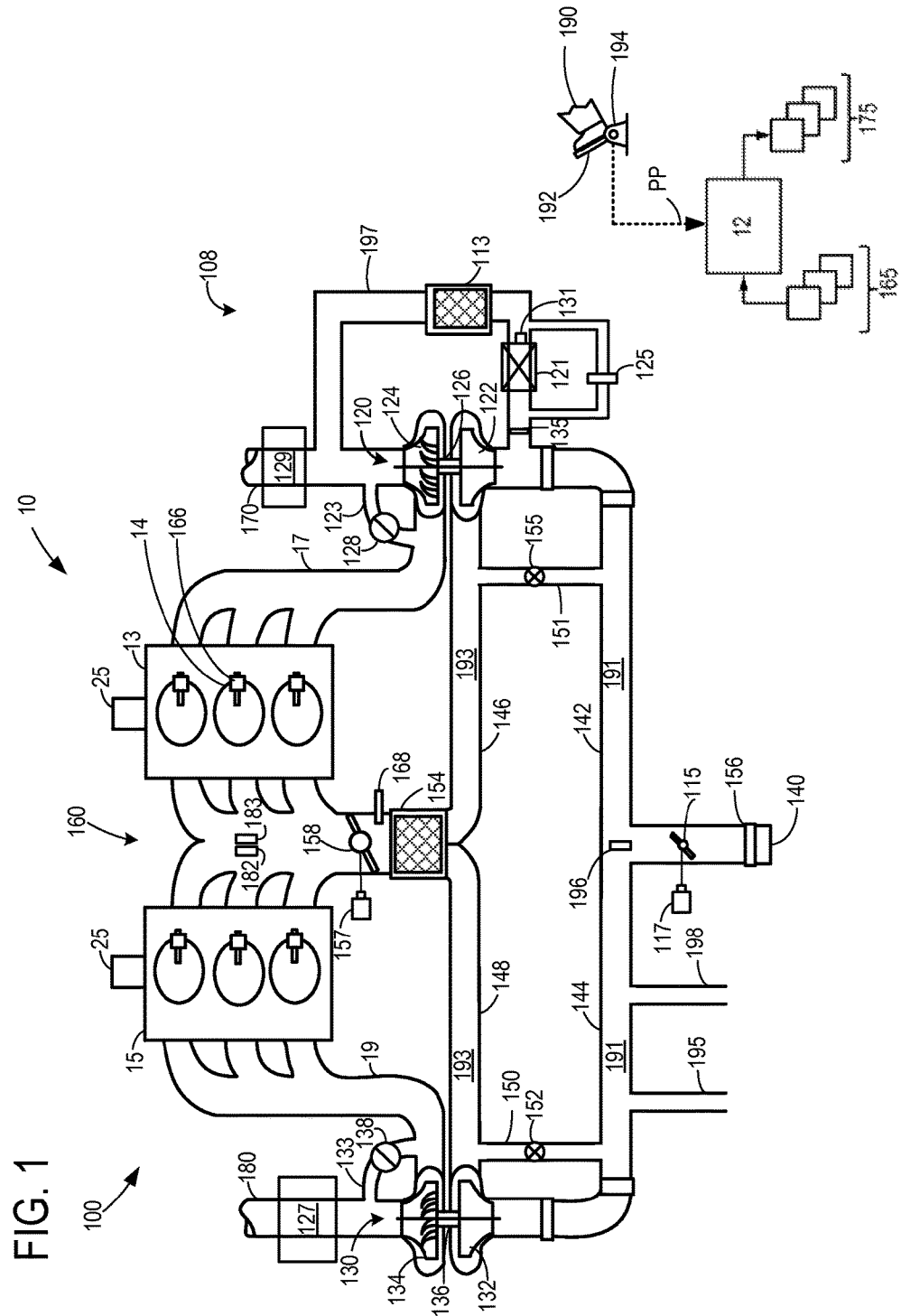
FIGS. 1-2 are schematic diagrams of an engine system.
Figure 2:
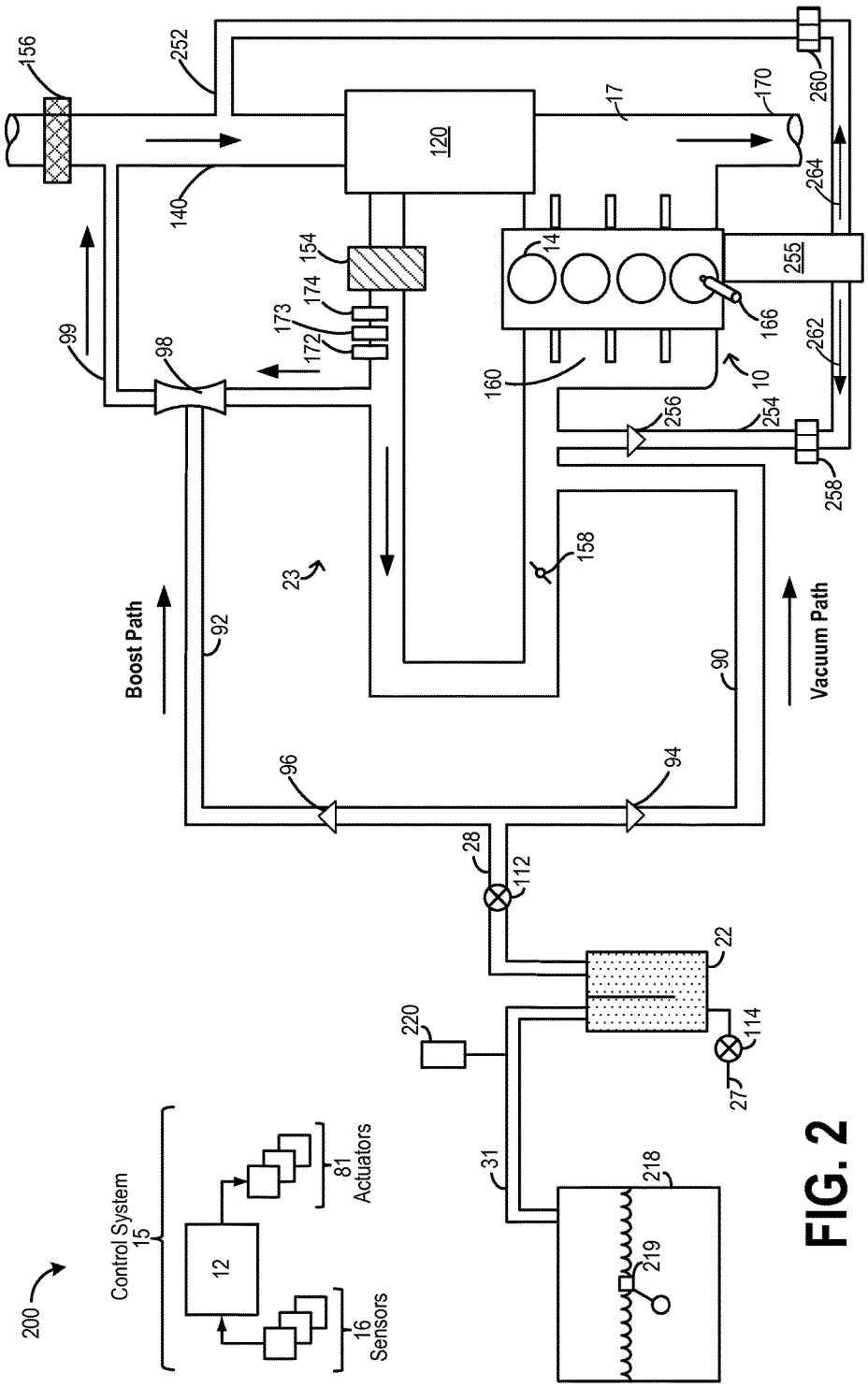
Figure 3:
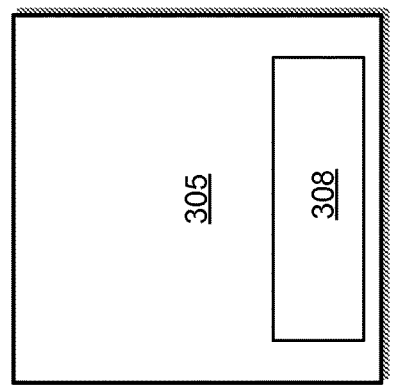
FIG. 3 illustrates a vehicle and example analyzer.
Figure 3:
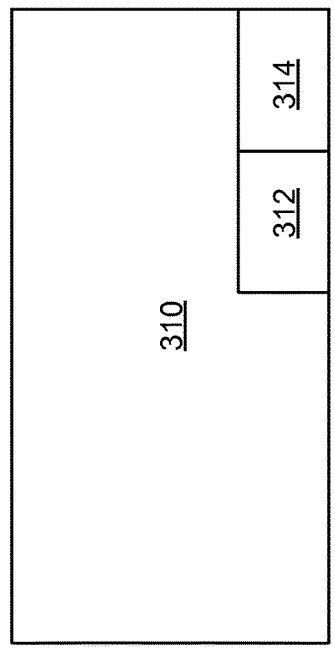

The following description relates to systems and methods for determining speciation of fuel in engine oil. Further, the following description includes estimating an impact of PCV hydrocarbons on an output of an oxygen sensor, such as an intake air oxygen sensor (IAO2). FIGS. 1-2 show example engines including a low-pressure exhaust gas recirculation (EGR) passage, a PCV system, and an intake oxygen sensor positioned in an intake passage downstream from the inlet of the LP-EGR passage and the inlet of the PCV system (during boosted operation) to the intake passage. FIG. 3 shows a vehicle and analyzer, such as a gas chromatography-mass spectrometer (GC-MS). FIG. 4 shows a method for analyzing an oil sample and determining a fuel dilution of the oil. FIG. 5 shows a method for characterizing various fuel species characteristics. FIG. 6 shows a method for estimating a fuel species impact on the intake oxygen sensor output. FIG. 7 shows a plot illustrating hydrocarbon accumulation in the engine oil and the hydrocarbons effect on the intake air oxygen sensor. FIG. 8 depicts a method for using an IAO2 sensor for estimating a fuel oil dilution while driving a vehicle.

FIG. 1 shows a schematic depiction of an example turbocharged engine including a multi-cylinder internal combustion engine 10 and twin turbochargers 120 and 130, which may be identical. As one non-limiting example, engine system 100 can be included as part of a propulsion system for a passenger vehicle. While not depicted herein, other engine configurations such as an engine with a single turbocharger may be used without departing from the scope of this disclosure.

Engine system 100 may be controlled at least partially by a controller 12 and by input from a vehicle operator 190 via an input device 192. In this example, input device 192 includes an accelerator pedal and a pedal position sensor 194 for generating a proportional pedal position signal PP. Controller 12 may be a microcomputer including the following: a microprocessor unit, input/output ports, an electronic storage medium for executable programs and calibration values (e.g., a read only memory chip), random access memory, keep alive memory, and a data bus. The storage medium read-only memory may be programmed with computer readable data representing non-transitory instructions executable by the microprocessor for performing the routines described herein as well as other variants that are anticipated but not specifically listed. Controller 12 may be configured to receive information from a plurality of sensors 165 and to send control signals to a plurality of actuators 175 (various examples of which are described herein). Other actuators, such as a variety of additional valves and throttles, may be coupled to various locations in engine system 100. Controller 12 may receive input data from the various sensors, process the input data, and trigger the actuators in response to the processed input data based on instruction or code programmed therein corresponding to one or more routines. Example control routines are described herein with regard to FIG. 8.

Engine system 100 may receive intake air via intake passage 140. As shown at FIG. 1, intake passage 140 may include an air filter 156 and an air induction system (AIS) throttle 115. The position of AIS throttle 115 may be adjusted by the control system via a throttle actuator 117 communicatively coupled to controller 12.

At least a portion of the intake air may be directed to a compressor 122 of turbocharger 120 via a first branch of the intake passage 140 as indicated at 142 and at least a portion of the intake air may be directed to a compressor 132 of turbocharger 130 via a second branch of the intake passage 140 as indicated at 144. Accordingly, engine system 100 includes a low-pressure AIS system (LP AIS) 191 upstream of compressors 122 and 132, and a high-pressure AIS system (HP AIS) 193 downstream of compressors 122 and 132.

A positive crankcase ventilation (PCV) conduit 198 (e.g., push-side pipe) may couple a crankcase (not shown) to the second branch 144 of the intake passage such that gases in the crankcase may be vented in a controlled manner from the crankcase. Further, evaporative emissions from a fuel vapor canister (not shown) may be vented into the intake passage through a fuel vapor purge conduit 195 coupling the fuel vapor canister to the second branch 144 of the intake passage.

The first portion of the total intake air can be compressed via compressor 122 where it may be supplied to intake manifold 160 via intake air passage 146. Thus, intake passages 142 and 146 form a first branch of the engine's air intake system. Similarly, a second portion of the total intake air can be compressed via compressor 132 where it may be supplied to intake manifold 160 via intake air passage 148. Thus, intake passages 144 and 148 form a second branch of the engine's air intake system. As depicted, intake air from intake passages 146 and 148 may not be recombined upstream of intake manifold 160. In some embodiments, additionally or alternatively, intake air from intake passages 146 and 148 can be recombined via a common intake passage before reaching intake manifold 160, where the intake air may be provided to the engine. In some examples, intake manifold 160 may include an intake manifold pressure sensor 182 for estimating a manifold pressure (MAP) and/or an intake manifold temperature sensor 183 for estimating a manifold air temperature (MCT), each communicating with controller 12. MAP sensor 182 may sense a manifold pressure to estimate a reference intake pressure.

In the depicted example, intake manifold 160 also includes a charge air cooler (CAC) 154 and a throttle 158. The position of throttle 158 may be adjusted by the control system via a throttle actuator 157 communicatively coupled to controller 12. As shown, throttle 158 may located downstream of CAC 154, and may be configured to adjust the flow of an intake gas stream entering engine 10.

As shown at FIG. 1, a compressor bypass valve (CBV) 152 may be arranged in CBV passage 150 and a CBV 155 may be arranged in CBV passage 151. In one example, CBVs 152 and 155 may be electronic pneumatic CBVs (EPCBVs). CBVs 152 and 155 may be controlled to enable release of pressure (e.g., compressor surge) in the intake system when the engine is boosted. An upstream end of CBV passage 150 may be coupled with intake passage 148 downstream of compressor 132, and a downstream end of CBV passage 150 may be coupled with intake passage 144 upstream of compressor 132. Similarly, an upstream end of a CBV passage 151 may be coupled with intake passage 146 downstream of compressor 122, and a downstream end of CBV passage 151 may be coupled with intake passage 142 upstream of compressor 122. Depending on a position of each CBV, air compressed by the corresponding compressor may be recirculated into the intake passage upstream of the compressor (e.g., intake passage 144 for compressor 132 and intake passage 142 for compressor 122). For example, CBV 152 may open to recirculate compressed air upstream of compressor 132 and/or CBV 155 may open to recirculate compressed air upstream of compressor 122 to release pressure in the intake system during selected conditions to reduce the effects of compressor surge loading. CBVs 155 and 152 may be either actively or passively controlled by the control system.

As shown, a compressor inlet pressure (CIP) sensor 196 is arranged in the intake passage 142. Among other functions, CIP sensor 196 may be used to determine a pressure downstream of an EGR valve 121.

Engine 10 may include a plurality of cylinders 14. In the depicted example, engine 10 includes six cylinders arrange in a V-configuration. Specifically, the six cylinders are arranged on two banks 13 and 15, with each bank including three cylinders. In alternate examples, engine 10 can include two or more cylinders such as 3, 4, 5, 8, 10 or more cylinders. These various cylinders can be equally divided and arranged in alternate configurations, such as V, in-line, boxed, etc. Each cylinder 14 may be configured with a fuel injector 166. In the depicted example, fuel injector 166 is a direct in-cylinder injector. However, in other examples, fuel injector 166 can be configured as a port based fuel injector.

Intake air supplied to each cylinder 14 (herein, also referred to as combustion chamber 14) may be used for fuel combustion and products of combustion may then be exhausted via bank-specific exhaust passages. In the depicted example, a first bank 13 of cylinders of engine 10 can exhaust products of combustion via a common exhaust passage 17 and a second bank 15 of cylinders can exhaust products of combustion via a common exhaust passage 19.

The position of intake and exhaust valves of each cylinder 14 may be regulated via hydraulically actuated lifters coupled to valve pushrods, or via mechanical buckets in which cam lobes are used. In this example, at least the intake valves of each cylinder 14 may be controlled by cam actuation using a cam actuation system. Specifically, the intake valve cam actuation system 25 may include one or more cams and may utilize variable cam timing or lift for intake and/or exhaust valves. In alternative embodiments, the intake valves may be controlled by electric valve actuation. Similarly, the exhaust valves may be controlled by cam actuation systems or electric valve actuation. In still another alternative embodiment, the cams may not be adjustable.

Products of combustion that are exhausted by engine 10 via exhaust passage 17 can be directed through exhaust turbine 124 of turbocharger 120, which in turn can provide mechanical work to compressor 122 via shaft 126 in order to provide compression to the intake air. Alternatively, some or all of the exhaust gases flowing through exhaust passage 17 can bypass turbine 124 via turbine bypass passage 123 as controlled by wastegate 128. The position of wastegate 128 may be controlled by an actuator (not shown) as directed by controller 12. As one non-limiting example, controller 12 can adjust the position of the wastegate 128 via pneumatic actuator controlled by a solenoid valve. For example, the solenoid valve may receive a signal for facilitating the actuation of wastegate 128 via the pneumatic actuator based on the difference in air pressures between intake passage 142 arranged upstream of compressor 122 and intake passage 146 arranged downstream of compressor 122. In other examples, other suitable approaches other than a solenoid valve may be used for actuating wastegate 128.

Similarly, products of combustion that are exhausted by engine 10 via exhaust passage 19 can be directed through exhaust turbine 134 of turbocharger 130, which in turn can provide mechanical work to compressor 132 via shaft 136 in order to provide compression to intake air flowing through the second branch of the engine's intake system. Alternatively, some or all of the exhaust gases flowing through exhaust passage 19 can bypass turbine 134 via turbine bypass passage 133 as controlled by wastegate 138. The position of wastegate 138 may be controlled by an actuator (not shown) as directed by controller 12. As one non-limiting example, controller 12 can adjust the position of wastegate 138 via a solenoid valve controlling a pneumatic actuator. For example, the solenoid valve may receive a signal for facilitating the actuation of wastegate 138 via the pneumatic actuator based on the difference in air pressures between intake passage 144 arranged upstream of compressor 132 and intake passage 148 arranged downstream of compressor 132. In other examples, other suitable approaches other than a solenoid valve may be used for actuating wastegate 138.

In some examples, exhaust turbines 124 and 134 may be configured as variable geometry turbines, wherein controller 12 may adjust the position of the turbine impeller blades (or vanes) to vary the level of energy that is obtained from the exhaust gas flow and imparted to their respective compressor. Alternatively, exhaust turbines 124 and 134 may be configured as variable nozzle turbines, wherein controller 12 may adjust the position of the turbine nozzle to vary the level of energy that is obtained from the exhaust gas flow and imparted to their respective compressor. For example, the control system can be configured to independently vary the vane or nozzle position of the exhaust gas turbines 124 and 134 via respective actuators.

Products of combustion exhausted by the cylinders via exhaust passage 19 may be directed to the atmosphere via exhaust passage 180 downstream of turbine 134, while combustion products exhausted via exhaust passage 17 may be directed to the atmosphere via exhaust passage 170 downstream of turbine 124. Exhaust passages 170 and 180 may include one or more exhaust after-treatment devices, such as a catalyst, and one or more exhaust gas sensors. For example, as shown at FIG. 1, exhaust passage 170 may include an emission control device 129 arranged downstream of the turbine 124, and exhaust passage 180 may include an emission control device 127 arranged downstream of the turbine 134. Emission control devices 127 and 129 may be selective catalytic reduction (SCR) devices, three way catalysts (TWC), $NO_x$ traps, various other emission control devices, or combinations thereof. Further, in some embodiments, during operation of the engine 10, emission control devices 127 and 129 may be periodically regenerated by operating at least one cylinder of the engine within a particular air/fuel ratio, for example.

Engine system 100 may further include one or more exhaust gas recirculation (EGR) systems for recirculating at least a portion of exhaust gas from the exhaust manifold to the intake manifold. These may include one or more high-pressure EGR systems for proving high pressure EGR (HP EGR) and one or more low-pressure EGR-loops for providing low pressure EGR (LP EGR). In one example, HP EGR may be provided in the absence of boost provided by turbochargers 120, 130, while LP EGR may be provided in the presence of turbocharger boost and/or when exhaust gas temperature is above a threshold. In still other examples, both HP EGR and LP EGR may be provided simultaneously.

In the depicted example, engine system 100 may include a low-pressure (LP) EGR system 108. LP EGR system 108 routes a desired portion of exhaust gas from exhaust passage 170 to intake passage 142. In the depicted embodiment, EGR is routed in an EGR passage 197 from downstream of turbine 124 to intake passage 142 at a mixing point located upstream of compressor 122. The amount of EGR provided to intake passage 142 may be varied by the controller 12 via EGR valve 121 coupled in the LP EGR system 108. In the example embodiment shown at FIG. 1, LP EGR system 108 includes an EGR cooler 113 positioned upstream of EGR valve 121. EGR cooler 113 may reject heat from the recirculated exhaust gas to engine coolant, for example. The LP EGR system may include a differential pressure over valve (DPOV) sensor 125. In one example, an EGR flow rate may be estimated based on the DPOV system which includes the DPOV sensor 125 that detects a pressure difference between an upstream region of the EGR valve 121 and a downstream region of EGR valve 121. EGR flow rate (e.g., LP EGR flow rate) determined by the DPOV system may be further based on an EGR temperature detected by an EGR temperature sensor 135 located downstream of EGR valve 121 and an area of EGR valve opening detected by an EGR valve lift sensor 131. In another example, EGR flow rate may be determined based on outputs from an EGR measurement system that includes an intake oxygen sensor 168, mass air flow sensor (not shown), manifold absolute pressure (MAP) sensor 182 and manifold temperature sensor 183. In some examples, both the EGR measurement systems (that is, the DPOV system including differential pressure sensor 125 and the EGR measurement system including intake oxygen sensor 168) may be used to determine, monitor, and adjust EGR flow rate.

In an alternate embodiment, the engine system may include a second LP EGR system (not shown) that routes a desired portion of exhaust gas from exhaust passage 180 to intake passage 144. In another alternate embodiment, the engine system may include both the LP EGR systems (one routing exhaust gas from exhaust passage 180 to intake passage 144, and another routing exhaust gas from exhaust passage 170 to intake passage 142) described above.

EGR valve 121 may be configured to adjust an amount and/or rate of exhaust gas diverted through the corresponding EGR passages to achieve a desired EGR dilution percentage of the intake charge entering the engine, where an intake charge with a higher EGR dilution percentage includes a higher proportion of recirculated exhaust gas to air than an intake charge with a lower EGR dilution percentage. In addition to the position of the EGR valves, it will be appreciated that AIS throttle position of the AIS throttle 115, and other actuators may also affect the EGR dilution percentage of the intake charge. As an example, AIS throttle position may increase the pressure drop over the LP EGR system, allowing more flow of LP EGR into the intake system. As a result, this may increase the EGR dilution percentage, whereas less LP EGR flow into the intake system may decrease the EGR dilution percentage (e.g., percentage EGR). Accordingly, EGR dilution of the intake charge may be controlled via control of one or more of EGR valve position and AIS throttle position among other parameters. Thus, adjusting one or more of the EGR valves 121 and the AIS throttle 115 may adjust and EGR flow amount (or rate) and subsequently a percentage EGR in the mass air flow (e.g., air charge entering the intake manifold).

The engine 10 may further include one or more oxygen sensors positioned upstream of throttle 158. As such, the one or more oxygen sensors may be referred to as intake oxygen sensors. In the depicted embodiment, an intake air oxygen (IAO2) sensor 168 is positioned upstream of throttle 158 and downstream of CAC 154. However, in other embodiments, intake oxygen sensor 168 may be arranged at another location, such as upstream of the CAC 154 in one or more of intake passages 146 and 148. Intake oxygen sensor (IAO2) 168 may be any suitable sensor for providing an indication of the oxygen concentration of the intake charge air, such as a linear oxygen sensor, intake UEGO (universal or wide-range exhaust gas oxygen) sensor, two-state oxygen sensor, etc. In one example, the intake oxygen sensors 168 may be an intake oxygen sensor including a heated element as the measuring element. During operation, a pumping current of the intake oxygen sensor may be indicative of an amount of oxygen in the gas flow.

Intake oxygen sensor 168 may be used for estimating an intake oxygen concentration and inferring an amount of EGR flow through the engine based on a change in the intake oxygen concentration upon opening of the EGR valve 121. Specifically, a change in the output of the sensor upon opening the EGR valve 121 is compared to a reference point where the sensor is operating with no EGR (the zero point). Based on the change (e.g., decrease) in oxygen amount from the time of operating with no EGR, an EGR flow currently provided to the engine can be calculated. For example, upon applying a reference voltage (Vs) to the sensor, a pumping current (Ip) is output by the sensor. The change in oxygen concentration may be proportional to the change in pumping current (delta Ip) output by the sensor in the presence of EGR relative to sensor output in the absence of EGR (the zero point). Based on a deviation of the estimated EGR flow from the expected (or target) EGR flow, further EGR control may be performed.

A zero point estimation of the intake oxygen sensor 168 may be performed during idle conditions where intake pressure fluctuations are minimal and when no PCV or purge air is ingested into the low pressure induction system. In addition, the idle adaptation may be performed periodically, such as at every first idle following an engine start, to compensate for the effect of sensor aging and part-to-part variability on the sensor output.

A zero point estimation of the intake oxygen sensor may alternatively be performed during engine non-fueling conditions, such as during a deceleration fuel shut off (DFSO). By performing the adaptation during DFSO conditions, in addition to reduced noise factors such as those achieved during idle adaptation, sensor reading variations due to EGR valve leakage can be reduced.

Now turning to FIG. 2, another example embodiment 200 of the engine of FIG. 1 is shown. As such, components previously introduced in FIG. 1 are numbered similarly and not re-introduced here for reasons of brevity.

Embodiment 200 shows a fuel tank 218 configured to deliver fuel to engine fuel injectors. A fuel pump (not shown) immersed in fuel tank 218 may be configured to pressurize fuel delivered to the injectors of engine 10, such as to injector 166. Fuel may be pumped into the fuel tank from an external source through a refueling door (not shown). Fuel tank 218 may hold a plurality of fuel blends, including fuel with a range of alcohol concentrations, such as various gasoline-ethanol blends, including E10, E85, gasoline, etc., and combinations thereof. A fuel level sensor 219 located in fuel tank 218 may provide an indication of the fuel level to controller 12. As depicted, fuel level sensor 219 may comprise a float connected to a variable resistor. Alternatively, other types of fuel level sensors may be used. One or more other sensors may be coupled to fuel tank 218 such as a fuel tank pressure transducer 220 for estimating a fuel tank pressure.

Vapors generated in fuel tank 218 may be routed to fuel vapor canister 22, via conduit 31, before being purged to engine intake 23. These may include, for example, diurnal and refueling fuel tank vapors. The canister may be filled with an appropriate adsorbent, such as activated charcoal, for temporarily trapping fuel vapors (including vaporized hydrocarbons) generated in the fuel tank. Then, during a later engine operation, when purge conditions are met, such as when the canister is saturated, the fuel vapors may be purged from the canister into the engine intake by opening canister purge valve (CPV) 112 and canister vent valve 114.

Canister 22 includes a vent 27 for routing gases out of the canister 22 to the atmosphere when storing, or trapping, fuel vapors from fuel tank 218. Vent 27 may also allow fresh air to be drawn into fuel vapor canister 22 when purging stored fuel vapors to engine intake 23 via purge lines 90 or 92 (depending on boost level) and purge valve 112. While this example shows vent 27 communicating with fresh, unheated air, various modifications may also be used. Vent 27 may include a canister vent valve 114 to adjust a flow of air and vapors between canister 22 and the atmosphere. The vent valve 114 may be opened during fuel vapor storing operations (for example, during fuel tank refueling and while the engine is not running) so that air, stripped of fuel vapor after having passed through the canister, can be pushed out to the atmosphere. Likewise, during purging operations (for example, during canister regeneration and while the engine is running), the vent valve may be opened to allow a flow of fresh air to strip the fuel vapors stored in the canister.

Fuel vapors released from canister 22, for example during a purging operation, may be directed into engine intake manifold 160 via purge line 28. The flow of vapors along purge line 28 may be regulated by canister purge valve 112, coupled between the fuel vapor canister and the engine intake. The quantity and rate of vapors released by the canister purge valve 112 may be determined by the duty cycle of an associated canister purge valve solenoid (not shown). As such, the duty cycle of the canister purge valve solenoid may be determined by the vehicle's powertrain control module (PCM), such as controller 12, responsive to engine operating conditions, including, for example, engine speed-load conditions, an air-fuel ratio, a canister load, etc. The duty cycle may include a frequency (e.g., rate) of opening and closing the canister purge valve 112.

An optional canister check valve (not shown) may be included in purge line 28 to prevent intake manifold pressure from flowing gases in the opposite direction of the purge flow. As such, the check valve may be necessary if the canister purge valve control is not accurately timed or the canister purge valve itself can be forced open by a high intake manifold pressure. An estimate of the manifold absolute pressure (MAP) may be obtained from MAP sensor 182 coupled to intake manifold 160 and communicated with controller 12. Alternatively, MAP may be inferred from alternate engine operating conditions, such as mass air flow (MAF), as measured by a MAF sensor coupled to the intake manifold.

Purge hydrocarbons may be directed to intake manifold 160 via either a boost path 92 or a vacuum path 90 based on engine operating conditions. Specifically, during conditions when turbocharger 120 is operated to provide a boosted aircharge to the intake manifold, the elevated pressure in the intake manifold causes one-way valve 94 in the vacuum path 90 to close while opening one-way valve 96 in the boost path 92. As a result, purge air is directed into the air intake passage 140, downstream of air filter 156 and upstream of charge air cooler 154 via the boost path 92. Herein, the purge air is introduced upstream of intake oxygen sensor 168. In some embodiments, as depicted, a venturi 98 may be positioned in the boost path such that the purge air is directed to the intake upon passing through the venturi 98 and passage 99. This allows the flow of purge air to be advantageously harnessed for vacuum generation.

During conditions when engine 10 is operated without boost, elevated vacuum in the intake manifold causes one-way valve 94 in the vacuum path to open while closing one-way valve 96 in the boost path. As a result, purge air is directed into the intake manifold 160, downstream of throttle 158 via the vacuum path 90. Herein, the purge air is introduced downstream of intake oxygen sensor 168.

PCV hydrocarbons may also be directed to intake manifold 160 via either a boost side PCV hose 252 or a vacuum side PCV hose 254 based on engine operating conditions. Specifically, blow-by gases from engine cylinders 14 flow past the piston rings and enter crankcase 255. During conditions when turbocharger 120 is operated to provide a boosted aircharge to the intake manifold, the elevated pressure in the intake manifold causes one-way valve 256 in vacuum side PCV hose 254 to close. As a result, during boosted engine operation, PCV gases flow in a first direction (arrow 264) and are received in the engine intake upstream of the intake oxygen sensor 168. Specifically, PCV air is directed into the air intake passage 140, downstream of air filter 156 and upstream of charge air cooler 154 via boost side PCV hose 252. The PCV flow may be directed to the intake passage 140 upon passage through a boost side oil separator 260. The boost side oil separator 260 may be integrated into the cam cover or may be an external component. Thus, during boosted conditions, the PCV gases are introduced upstream of intake oxygen sensor 168 and therefore do affect the output of oxygen sensor 168. The boosted conditions may include intake manifold pressure above ambient pressure.

In comparison, during conditions when engine 10 is operated without boost, elevated vacuum in the intake manifold causes one-way valve 256 in the vacuum side PCV hose 254 to open. As a result, during non-boosted engine operating, PCV gases flow in a second direction (arrow 262) different from the first direction and are received in the engine intake downstream of the intake oxygen sensor 168. In the depicted example, the second direction of PCV flow during non-boosted engine operation is opposite of the first direction of PCV flow during boosted engine operation (compare arrows 262 and 264). Specifically, during non-boosted operation, PCV air is directed into the intake manifold 160, directly, downstream of throttle 158 via the vacuum side PCV hose 254. The PCV flow may be directed to the intake manifold 160 upon passage through a vacuum side oil separator 258. Herein, the PCV air is introduced downstream of intake oxygen sensor 168, and therefore does not affect the output of oxygen sensor 168. Thus, due to the specific engine configuration, during boosted engine operation, PCV and purge air hydrocarbons are ingested into the engine intake manifold upstream of the intake oxygen sensor 168 and are ingested into the engine intake manifold downstream of the intake oxygen sensor 168 during non-boosted conditions.

As previously discussed, the intake air oxygen sensor 168 can be used to measure the amount of EGR in the intake aircharge as a function of the amount of change in oxygen content due to the addition of EGR as a diluent. Thus, as more EGR is introduced, the sensor may output a reading or pumping current corresponding to a lower oxygen concentration. During the estimation, a nominal reference voltage (e.g., at 450 mV), or Nernst voltage, is applied to the sensor and an output (e.g., a pumping current output by the sensor upon application of the lower reference voltage) is noted. Based on the output of the sensor relative to a zero point of the sensor (that is, sensor output at no EGR conditions), a change in oxygen concentration is learned, and an intake dilution with EGR is inferred.

However, if the EGR estimation is performed during conditions when purging and/or crankcase ventilation is enabled (e.g., PCV flow is enabled), an output of the sensor is corrupted. Said another way, PCV flow (which may include fuel vaporized from the engine oil) and/or fuel vapor purge flow may cause an error in the output of the intake oxygen sensor. As such, purge air and/or positive crankcase ventilation hydrocarbons (e.g., PCV flow) may be ingested during boosted engine operating conditions along boost path 92 and boost side PCV hose 252 when the purge valve 112 is open and/or the PCV valve 256 is closed. The sensor output may be corrupted primarily due to the ingested hydrocarbons reacting with ambient oxygen at the sensing element of the intake sensor. This reduces the (local) oxygen concentration read by the sensor. Since the output of the sensor and the change in oxygen concentration is used to infer an EGR dilution of intake aircharge, the reduced oxygen concentration read by the intake oxygen sensor in the presence of purge air and/or PCV may be incorrectly interpreted as additional diluent. This impacts the EGR estimation and the subsequent EGR control. Specifically, EGR may be over-estimated.

FIG. 3 depicts system 300 illustrating a vehicle 305 and an analyzer 310. In examples described herein, the analyzer may sample an engine fluid from the vehicle, such as engine oil, and provide data regarding compounds in the fluid sample to determine fuel dilution in engine oil based on speciation of hydrocarbons in fuel in the engine oil.

As described above, a vehicle 305 may comprise an engine (e.g., engine 10) to power the vehicle 305. The engine may comprise one or more cylinders (e.g., combustion chamber(s) 30) configured to receive fuel via one or more direct injectors, for example. The injected fuel may impinge on a cylinder wall and drip into a crankcase of the engine, collecting in an oil sump 308 of the crankcase. The fuel may then vaporize from the crankcase and affect an IAO2 measurement during PCV purge, as explained above. The hydrocarbon species that accumulate in the oil and that evaporate into the crankcase may differ from the hydrocarbon species present in the injected fuel, and these various species may differentially impact intake oxygen sensor output, for example. For example, the difference may occur due to hydrocarbons less prone to combustion (e.g., heavy chain hydrocarbons that are less volatile and thus more likely to impinge on cylinder walls) not combusting, while hydrocarbons more prone to combustion (e.g., light-chain hydrocarbons that are more volatile and thus more likely to vaporize even during cold engine conditions) combusting during a combustion phase of an engine cycle. In this way, the heavy chain hydrocarbons may accumulate in the oil in the crankcase. Heavy-chain and light-chain hydrocarbons will be discussed in more detail below.

In order to determine the speciation of the fuel dilution into the oil, engine fluid (such as engine oil) may be sampled and analyzed via the analyzer 310. In one example, the analyzer may comprise a gas chromatographer. The analyzer may additionally comprise a mass spectrometer to form a GC-MS analyzer. It will be appreciated that other suitable analyzers may be used, such as a gas chromatography-flame ionization detectors. Additionally or alternatively, the GC-MS may be separated, in that a GC and a MS may be used. For a separate GC and MS, two identical samples of oil may be used to analyze a fuel in oil dilution. This is due to combustion of the sample in both the GC and the MS.

The analyzer 310 may include a computing device 312 having a processor and a memory device storing instructions executable by the processor. The memory device may be programmed with computer readable data representing non-transitory instructions executable by the processor for performing the methods and routines described herein as well as other variants that are anticipated but not specifically listed. The computing device 312 may be operatively coupled to a display device 314 such that image information may be sent from computing device 312 for display via display device 314. The computing device 312 may further be configured to receive input from a user input device (not shown), such as a mouse, keyboard, touch screen, etc. Additionally, the computing device 312 may be operatively coupled with various sensors, such as an engine oil temperature sensor, engine oxygen sensor, or other sensors.

The instructions stored on computing device 312 may be executable to receive output from the analyzer (e.g., GC-MS data) in order to determine one or more retention times of a sampled engine fluid, or other suitable information, and determine which of a plurality of hydrocarbon species are present in the sampled engine fluid, as explained in more detail below. The display device 314 may display an indication of the information output from the computing device 312.

An example method for determining speciation of fuel in engine oil with a GC-MS analyzer and computing device is presented below. An oil sample may be taken from the oil sump of a crankcase of an engine and mixed with a suitable solvent and/or desired internal standard, such as dichloromethane as a solvent and n-hexadecane as an internal standard. The sample is injected into a port of the GC-MS. The sample initially flows through the GC where it is vaporized and passes over a column of the GC. The column allows compounds of varying sizes to separate from one another. As the compounds traverse the column, they pass through the GC and eventually elute out of the column, the timing of which elution is determined and stored as a retention time. After detecting a retention time for each compound, the separated compounds flow through a mass spectrometer to be bombarded by electrons. The electrons are able to cleave bonds within individual hydrocarbons such that the hydrocarbons may fragment. The fragmentation of the hydrocarbon is based on a fragment's stability (e.g., its ability to stabilize a positive charge due to the loss of an electron during the electron bombardment). The fragments are then captured by a detector to provide a mass-to-charge ratio. Total fuel content may be estimated from the total ion count for all gasoline-range peaks and the corresponding response for the n-hexadecane internal standard.

The retention time may correlate to a molecular weight of a compound, in which the retention time may increase as the molecular weight increases. Additionally or alternatively, the retention time may increase as a boiling point of a compound increases. Therefore, smaller, lighter compounds may traverse the column faster than larger heavier compounds (e.g., lower retention time). The sampled engine oil may have multiple fractions each with an associated retention time and total MS ion count, which may be used to identify the hydrocarbon species within the engine oil, as explained below.

As the sample passes through the GC, it condenses to then be passed through the mass spectrometer. The compound is inundated with electrons via an electron beam and fragments into charged, radical fragments of the original compound (e.g., parent compound). The parent compound fragments based on stability. For example, a compound may produce more of a more stable fragment as opposed to creating a less stable fragment. The fragments are then analyzed by the mass spectrometer and a molecular weight of for each individual fragment is provided. Analysis of the molecular weight of the fragments may lead to the parent compound via identifying fragmentation patterns based on the most stable fragments the parent compound may produce. The molecular weight may then be correlated to a retention time via its molecular weight, boiling point, and a comparison to an analysis of a pure sample. For example, if the oil sample provides a molecular weight of 92 then it may be assumed toluene is present in the oil. However, for definitive evidence, a pure sample of toluene may be injected into the GC-MS in order to compare the results between the pure toluene and the compound assumed to be toluene in the oil sample.

While the GC-MS analysis described above may provide information usable to determine which compounds are present in the engine oil, differentiating the retention times and molecular weights from the sampled oil from all possible retention times and molecular weights of all possible compounds may be process and time intensive. To simplify the identification of the species present in the engine oil, the retention times of the sampled oil may be input into a model that includes a plurality of equations derived from GC-MS data collected from a set of known hydrocarbon species. For example, a look-up table including properties of 75 known hydrocarbons may be stored on the computing device. The properties for each HC species may include retention time, molecular weight, boiling point, and other properties. The model may include a set of equations derived from the look-up table data in order to determine the boiling point, vapor pressure, etc., for each species in the sampled oil. The model may output an indication of which hydrocarbon species are present in the sampled oil and at what concentration. Further, by including engine parameters determined at the time of sampling, such as crankcase pressure, the concentration of the hydrocarbon species that have evaporated out of the engine oil and into the crankcase may be determined as well as the impact of each species on an oxygen sensor, such the intake air oxygen sensor described above. The creation of the model as well as an example of how the model is applied are described below with respect to FIGS. 4-6.

Turning now to FIG. 4, a high level flow chart illustrating a method 400 for determining speciation of fuel in an engine fluid sample, such as engine oil sampled from a crankcase oil sump, is illustrated. Method 400 may be executed by a computing device configured to receive output from an analyzer, such as computing device 312 of FIG. 3, in combination with various sensors, input devices, output devices, and/or actuators, such as an analyzer (e.g., analyzer 310 of FIG. 3), display device, etc. While method 400 and subsequent methods are described with respect to sampled engine oil, it is to be understood that other fluids may be sampled, such as fuel in a fuel tank, oil present in locations other than the oil sump, intake air, exhaust gas, etc.

Method 400 begins at 402, where an oil sample obtained from an engine crankcase is injected into a GC-MS, as described above. The method 400 proceeds to 404 to apply the data output by the GCMS to a model. As explained above, the data output by the GCMS may include a retention time and corresponding MS ion count for each fraction of the oil sample. The model is stored on and executed by a computing device operatively coupled to the GCMS, such as computing device 312 of FIG. 3. The GCMS output data and/or output from the model may be used to identify each hydrocarbon species present in the sampled oil, as well as the relative concentration of each identified species and overall fuel content of the sampled oil. The model includes a plurality of equations that may be used to determine the impact of each identified species on an oxygen sensor. As indicated at 406, the model may be derived by plotting the boiling point, molecular weight, vapor pressure, and the number of oxygen atoms burning with a known hydrocarbon at stoichiometric conditions as a function of GCMS retention time for a set of known HCs and fitting equations to each plot. Additionally, each identified HC species may be classified as being aromatic or non-aromatic. Furthermore, each HC may be determined to be a light-chain (e.g., less than 100 g/mol), medium-chain (e.g., 100 g/mol to 175 g/mol), or heavy-chain (e.g., greater than 175 g/mol).

Further, fuel vapors may be present in the PCV flow due to evaporation of the fuel vapors out of engine oil housed in an oil sump of the crankcase, despite nominal engine operating temperatures (e.g., 80-96° C.) being lower than the boiling point of the hydrocarbons in the engine oil. This may be due to a vapor pressure phenomenon rather than a boiling phenomenon, as volatility of a molecule increases as its temperature increases. Additionally, as the vapor pressure of a compound increases, its boiling point decreases. Therefore, light-chain hydrocarbons may evaporate from the oil in the crankcase before medium-chain or heavy-chain hydrocarbons.

At 408, the output of the model is displayed, such as on a display device operatively coupled to the computing device (e.g., display device 314 of FIG. 3). The output of the model may include the evaporation rate of the hydrocarbon species in the sampled oil and/or the oxygen sensor impact of the sampled oil as well as the evaporated hydrocarbons in the gaseous phase surrounding the oil sump (e.g., in the crankcase) and/or each hydrocarbon species within the sampled oil, as indicated at 410. Additionally or alternatively, the model may output the speciation of the fuel in the sampled oil and/or in the vapors of the crankcase housing the oil sump.

In some examples, the oxygen sensor impact may be used to calibrate an oxygen sensor present in the vehicle. For example, the computing device may receive a measurement of oxygen concentration from the on-vehicle oxygen sensor at substantially the same time as the oil from the vehicle is sampled and when the oxygen sensor is exposed to crankcase vapors (such as during PCV purge conditions if the oxygen sensor is an intake oxygen sensor, or during DFSO if the oxygen sensor is an exhaust sensor). The oxygen sensor measurement may be compared to an expected oxygen concentration that is based on the predicted oxygen sensor effect of the hydrocarbons in the sampled oil as output above. For example, the expected oxygen concentration may be ambient air oxygen concentration corrected by the output oxygen sensor impact. If the measured oxygen concentration is different than the expected oxygen concentration, it may indicate the oxygen sensor is degraded. In other examples, the oxygen sensor may be calibrated such that the measured oxygen concentration matches the expected oxygen concentration. The calibration may include applying a correction factor to the output from the oxygen sensor, adjusting a gain of the oxygen sensor, or the like.

Thus, method 400 determines the speciation of fuel in an oil sample and estimates the impact of the fuel species evaporating out of the oil sample and into the crankcase on an oxygen sensor that may detect the crankcase vapors, such as an intake air oxygen sensor (which may sample PCV vapors during PCV purge) or an exhaust oxygen sensor (which may sample PCV vapors during PCV purge while operating under DFSO, for example). In some examples, method 400 may be performed multiple times under various engine operating parameters to determine the oxygen sensor impact as engine operating parameters change. For example, engine oil may be sampled during and/or after one or more engine drive cycles (e.g., consecutively driving cycles 505 and US-06 multiple times) in order to correlate oxygen sensor impact with engine cold start conditions, during engine warm-up, during typical light-load highway operation (when fuel may be more likely to evaporate out of the oil), or other operating conditions.

By determining if a HC is light-chain, medium-chain, and heavy-chain it may be determined if a hydrocarbon may be present in an engine oil based on operating conditions. For example, during a cold-start all three chains may be present in the crankcase engine oil. However, after reaching a threshold engine temperature (e.g., 80° C.) only medium-chain and/or heavy-chain hydrocarbons may be present in the crankcase oil. Additionally or alternatively, particular types of heavy-chain hydrocarbon may not vaporize out of the crankcase oil and may remain in the engine until an engine oil change occurs.

Additional details regarding derivation of the model as well as how the GCMS data may be applied to the model are presented below with respect to FIGS. 5-6. Using the IAO2 sensor to detect fuel in the crankcase oil will be discussed in more detail with respect to FIG. 8.

Turning now to FIG. 5, a method 500 for calculating characteristics of a hydrocarbon via the model discussed above with respect to FIG. 4 is illustrated. As explained above, the model includes a plurality of equations that relate GCMS retention time to various parameters, including boiling point, vapor pressure, etc., that may be used to estimate the evaporation rate of the hydrocarbon species out of the sampled engine oil and ultimately the impact of the species on an oxygen sensor. Before describing method 500 in detail, these equations are described below.

It should be understood that the correlation of measured retention times to boiling point, vapor pressure, etc., described below, includes equations derived from plots of retention times of a known set of hydrocarbons. GC retention times are not a fundamental physical property of the HCs (unlike boiling point, density, etc.). Rather, GC retention times are dependent on the GC column type and length, the GC oven temperature schedule, and other parameters. GC retention times, however, will generally be constant for a given GC column and operating conditions. As such, when different GC columns or other operating conditions are utilized, different retention times for the same hydrocarbon may be observed. In such circumstances, the below equations may be adapted based on the retention times of the known hydrocarbons as measured by the different GC column.

$$T_{BP}=aRT^2+bRT+c;\ a=-0.574,\ b=36.1,\ c=-253 \qquad \text{Equation 1}$$

Equation 1, which estimates a HC boiling point based on a retention time, was calculated by plotting the retention time and boiling point for at least 75 known hydrocarbons. The retention times ranged from 9 minutes to 27 minutes. The boiling points ranged from 25° C. to 300° C. In this way, a line of best fit was calculated for the plot in order to determine equation 1. By doing this, if a retention time is obtained while measuring an oil sample that does not correspond to a known compound, the unknown compound may be characterized further in order to determine the unknown compounds identity.

$$MW=9.5RT-13.9 \qquad \text{Equation 2}$$

Equation 2, which includes calculating a molecular weight based on a retention time, was calculated by plotting the retention time and molecular weights of the 75 known compounds. The molecular weights ranged from 70 g/mol to 250 g/mol. A line of best fit was calculated for the plot in order to determine equation 2. By doing this, if a retention time is obtained while measuring an oil sample that does not correspond to a known compound, the unknown compound may be characterized further in order to determine the unknown compounds identity. It may be preferred to calculate the MW of an unknown compound when only a GC is used to analyze an oil sample and/or when it may be difficult to construe a parent molecule from a fragment pattern.

$$\log(VP) = A + \frac{B}{T} + C\log(T) + DT^E \qquad \text{Equation 3}$$

Equation 3 was obtained from DIPPR (Design Institute for Physical Properties) database to calculate the vapor pressure of each one of the 75 compounds as a function of temperature. Constants A, B, C, D, and E are HC-specific, and vary between the different selected hydrocarbons.

$$\log(VP)_{T=40\,C} = \frac{p_1}{RT^4} + \frac{p_2}{RT^3} + \frac{p_3}{RT^2} + \frac{p_4}{RT} + p_5 \qquad \text{Equation 4}$$

$$p_1 = -8792,\ p_2 = 46208,\ p_3 = -8104.2,$$

$$p_4 = 642.51,\ \text{and}\ p_5 = -15.788$$

At a given temperature (e.g., 40° C.), the vapor pressure for all 75 compounds was plotted as a function of retention time. Equation 4 was obtained by fitting this relation, and constants p1, p2, p3, p4, and p5 were obtained for that specific temperature.

In this way, an unknown compound's vapor pressure at a constant temperature may be calculated based on its retention time. The values of $p_1$ to $p_5$ may vary as the temperature changes.

$$C_xH_y + \left(x+\frac{y}{4}\right)O_2 + \text{heat} \rightarrow (x)CO_2 + \left(\frac{y}{2}\right)H_2O + \text{heat} \qquad \text{Equation 5}$$

$$IAO_2 = \left(x+\frac{y}{4}\right) * \sqrt{\frac{MW_{O_2}}{MW_{HC}}} \qquad \text{Equation 6}$$

Equation 6, which includes calculating an effect on an oxygen sensor, such as an IAO2 sensor, based a MW of a HC calculated with equation 2 and a balanced combustion reaction (equation 5), allows for determining an amount of oxygen consumed by a HC on an oxygen sensor during stoichiometric conditions. In equation 6, x represents the number of carbon atoms and y represents the number of hydrogen atoms of the hydrocarbon species. Equation 6 includes an adjustment to account for the expected effect of diffusion rate differences for oxygen and hydrocarbon into the catalytic element of the oxygen sensor. Additionally, the amount of oxygen consumed by the hydrocarbon on the sensor may depend on the aromaticity of the hydrocarbon. The variables x and y in equations 5 and 6 have a linear dependency on retention time, however this linear relation is different for aromatics and non-aromatics. This difference is demonstrated in equations 7a and 7b, which shows the effect on IAO2 for the two classes of hydrocarbons:

$$\{IAO2\}_{aromatics}=0.30RT+1.57 \qquad \text{Equation 7a}$$

$$\{IAO2\}_{non\text{-}aromatics}=0.24RT+3.5 \qquad \text{Equation 7b}$$

As will be explained in more detail below, the vapor pressure of a HC may be expanded to estimate a gaseous molar concentration of a HC which may then be used to calculate an effect of the HC on the oxygen sensor.

Method 500 may be executed by a computing device configured to receive output from an analyzer, such as computing device 312 of FIG. 3, in combination with various sensors/input devices and/or actuators/output devices. Method 500 begins at 502, which includes selecting a retention time for a fraction of an oil sample, which may include one or more hydrocarbon species. The retention time may be obtained from the GC-MS data, as described above with respect to FIG. 4 (e.g., the retention time may be one of a plurality of retention times obtained from GCMS analysis of an oil sample). Dodecane ($C_{12}H_{26}$) may be used as an example hydrocarbon included in an oil sample for the entirety of FIG. 5. At 506, the method 500 includes using equation 1 to estimate a boiling point of the fuel species (e.g., an individual hydrocarbon compound) using its retention time at 508. In this way, the retention time of a compound may correspond to its boiling point. Using dodecane as an example, it has a retention time of 18.34, therefore according to equation 1 it has a boiling point of 216° C. As described above, this calculation may be especially useful for unknown compounds.

At 510, the method 500 includes using equation 2 to estimate a molecular weight of a hydrocarbon based on its retention time at 512. In this way, the retention time of a compound may correspond to its molecular weight. The molecular weight of a compound may correspond to its boiling point. As the molecular weight increases, the boiling point increases, and therefore, the vapor pressure of the compound decreases, as described above. For dodecane, equation 2 provides a molecular weight of 160.33. While the actual molecular weight of dodecane is 170.33, equation 2 provides an approximation of that value within a threshold range, such as less than 10% (for example, there is a 6% difference between the actual and calculated molecular weight of docedane). As described above, this calculation may be especially useful for unknown compounds. The molecular weight calculated in 512 may be later used with respect to FIG. 6.

At 514, the method 500 may use equation 4 to estimate a vapor pressure at 516 of a compound at a constant temperature. The constant temperature may be substantially equal to the sampled oil temperature measured by a temperature sensor. The values $p_1$ to $p_5$ were calculated at an engine oil temperature of 40° C. In some embodiments, these values may be similar or different for other temperatures. In this way, the vapor pressure of a hydrocarbon may be related to its current temperature (e.g., engine oil temperature), in which the vapor pressure increases as the current temperature of the engine oil increases. For dodecane, equation 4 provides a vapor pressure of 72.78 Pa. The vapor pressure calculated may be used later with respect to FIG. 6.

At 518, the method 500 includes using equation 6 to estimate the oxygen consumed by the hydrocarbon at stoichiometry at 520. As seen in equation 5, for a given hydrocarbon, 1 mol of carbon may consume 1 mole of oxygen while 1 mol of hydrogen may consume 0.25 moles of oxygen. Using dodecane as an example, equation 6 provides a response factor of 8.27 when the molecular weight of dodecane determined as a function of retention time is used (MW=160) and a response factor of 8.03 when the actual molecular weight of dodecane is used (MW=170). To improve the correlation between response factor and retention times, the hydrocarbon species were classified as aromatic or non-aromatic and equations derived for each classification of hydrocarbon, as shown by equations 7a and 7b. If dodecane is used again as example for equation 7b (as it is not aromatic), the response factor decreases to 7.9. The oxygen sensor effect value may be used later with respect to FIG. 6.

Thus, method 500 of FIG. 5 determines the boiling point, molecular weight, vapor pressure, and the number of oxygen atoms consumed at stoichiometry for a given hydrocarbon species identified in an oil sample, via a GCMS retention time of the hydrocarbon species. The molecular weight, vapor pressure, and oxygen atoms consumed at stoichiometry may be used to estimate how much of the hydrocarbon species evaporates out of the oil and into the air surrounding the oil sump from which the oil was sampled, and also estimate how much the evaporated hydrocarbon species will affect an oxygen sensor reading, as explained below.

Turning now to FIG. 6, a flow chart illustrates a method 600 for determining a molar concentration of a hydrocarbon in an engine oil and therefore estimate an effect of the hydrocarbon on an oxygen sensor. Method 600 may be executed by a computing device configured to receive output from an analyzer, such as computing device 312 of FIG. 3, in combination with one or more sensors, input devices, actuators, and/or output devices. The method 600 may further include totaling an effect of each individual hydrocarbon to determine a net total effect of the hydrocarbons in the engine oil on the intake oxygen sensor during a current engine operation.

Method 600 begins at 602, which includes determining, estimating, and/or measuring sampling parameters. The sampling parameters include but are not limited to sampled oil temperature, pressure in the housing surrounding the oil sump (e.g., crankcase pressure), engine drive cycle parameters at or before sampling, and/or other parameters. At 604, the method includes obtaining a GCMS retention time from an oil sample, as described above. Briefly, the oil sample may be obtained from a crankcase oil sump and analyzed via GCMS. The GCMS data may include a plurality of retention times, each corresponding to a given fraction of the oil sample. The analysis described below may be performed for each obtained retention time. At 606, the method includes determining the identity and type of hydrocarbon by comparing the measured retention time to retention times stored in a look-up table. The look-up table may output other information (e.g., aromaticity and size) for each hydrocarbon species.

At 608, the method 600 includes estimating a hydrocarbon percent by weight in the engine oil. The hydrocarbon percent by weight in the engine oil may be determined via injecting an oil sample into a gas chromatography-mass spectrometer (GC-MS). The GC-MS provides percent composition peaks for both the oil and the hydrocarbons via the gas chromatograph portion of the GC-MS. The percentages for the hydrocarbons are totaled in order to provide the hydrocarbon percent by weight in the oil.

At 610, the method 600 includes estimating the molar fraction of the hydrocarbon in the oil via equation 8 and the MW of the HC provided by equation 2.

$$x_{HC}^{liq} = \frac{MW_{oil}}{MW_{HC}} xw_{HC}^{liq} \qquad \text{Equation 8}$$

In equation 8, w represents a mass fraction (e.g., fraction of the total oil or fuel dilution sample by weight of a give hydrocarbon species) which may be obtained from the GCMS results. As explained above, aromatic and non-aromatic hydrocarbon species differentially effect oxygen sensors, and thus prior to performing the calculation of equation 8 and all remaining calculations, the identified hydrocarbon species may be classified as either being aromatic or non-aromatic. Then, the mass fraction for all aromatic species may be determined and the mass fraction for all non-aromatic species determined. Equation 8 utilizes a molecular weight value provided for the hydrocarbon by equation 2, the molecular weight of the oil, and the mass fraction to estimate the molar fraction of the hydrocarbon. The molar fraction represents the number of moles for the hydrocarbon divided by the total number of moles of hydrocarbons. In some examples, the molar fraction for each individual identified hydrocarbon species may be determined, while in other examples the molar fraction of all aromatic species and all non-aromatic species may be determined.

At 612, the method 600 includes estimating a partial pressure of the hydrocarbon via equation 9.

$$PP_{HC}^{gas} = X_{HC}^{liq} \times (VP)_{HC@Ti} \qquad \text{Equation 9}$$

In equation 9, the partial pressure of the hydrocarbon is estimated based on a product of the molar fraction and a vapor pressure of the hydrocarbon estimated by equation 4 with respect to FIG. 5. As described above, the vapor pressure is calculated at a specific engine oil temperature due to a vapor pressure of a compound being temperature dependent.

At 614, the method 600 includes calculating the molar fraction of the hydrocarbon in the gaseous phase via equation 10.

$$Y_{HC}^{gas} = \frac{Pp_{HC}^{gas}}{P_{ck}} \qquad \text{Equation 10}$$

In equation 10, $P_{ck}$ represents a total pressure of the crankcase. Y represents a molar fraction of the hydrocarbon in the gaseous phase. The molar fraction of the hydrocarbon in the gaseous phase may be defined as an amount of the hydrocarbon evaporated from the crankcase oil sump and mixing with other gases in the crankcase.

In one embodiment, $Y_{HC}^{gas}$ is may be used along with equation 6 to determine a number of moles of oxygen consumed by the hydrocarbon at 616 in the gaseous phase to produce carbon dioxide and water (e.g., Y represents a number of moles of the hydrocarbon in the gaseous phase). In this way, the effect of the hydrocarbon on the oxygen sensor may be estimated.

$$IAO2_{type\_effect} = Y_{type}^{gas} \times \{IAO2\}_{HCtype} \qquad \text{Equation 11}$$

At 616, the method 600 estimates an amount of oxygen consumed on a catalyst by vaporized hydrocarbons on the oxygen sensor using equation 11 and values provided by equation 6. The type effect on the oxygen sensor is based on the type of hydrocarbon (aromatic or non-aromatic). The $\{IAO2\}_{HCtype}$ is equal to equation 7a or 7b dependent on if the hydrocarbon is aromatic or non-aromatic.

At 618, the method 600 determines the impact of the hydrocarbon, in the engine oil, on the intake air oxygen sensor. The impact may corrupt the oxygen sensor reading and lead to the sensor reading an excess of EGR due to the vaporized hydrocarbons. In this way, the method 600 estimates and learns the impact of the HC on the oxygen sensor in order to maintain an EGR rate.

In some examples, the methods of FIGS. 4-6 may be performed over a variety of engine operating parameters in order to catalog the hydrocarbons present under each engine operating parameter into a look-up table to be stored in the memory of the engine controller. The catalog may include, for an individual HC, name, molecular weight, retention time, aromaticity, and type of chain. It will be appreciated by someone skilled in the art that the look-up table may comprise other suitable information regarding the HC, such as boiling point, vapor pressure, etc. Further, the look-up table may include a predicted effect on an oxygen sensor at each engine operating point. The engine operating points that may be referenced in the look-up table may include speed, load, engine temperature, time elapsed since engine start, and other parameters. In some examples, the operating points may include a rolling average, rate of change of each respective operating point over a given time period, or other suitable representation of the operating point.

This may be done such that a prediction may be made as to what type and amount of hydrocarbons are present in the crankcase oil during specific engine operating points. Further, an oxygen sensor of a vehicle may be used to determine a presence of HC in the crankcase oil during nominal engine operation. As such, an estimation of certain types of hydrocarbon located in the crankcase oil may be conducted via referencing data cataloged in the look-up table.

Turning now to FIG. 7, plot 700 illustrates a graph representing a fuel accumulation in engine oil during various engine temperatures. Plot 700 further illustrates graphs representing consumption of oxygen by the hydrocarbons at an oxygen sensor during various engine temperatures based on the type of hydrocarbon (aromatic or non-aromatic). It should be understood that the examples presented in FIG. 7 are illustrative in nature, and other outcomes are possible.

The graphs in FIG. 7 represent various operating parameters and resultant engine controls for determining a hydrocarbon impact on an oxygen sensor, such as an intake air oxygen sensor. The horizontal axes represent time and the vertical axes represent the respective engine condition being demonstrated. On plot 700, graph 702 represents a total non-aromatic hydrocarbon accumulation in an engine oil, graph 704 represents a total aromatic hydrocarbon accumulation in the engine oil, graph 706 represents a concentration of oxygen consumed by an evaporated aromatic hydrocarbon at the oxygen sensor, and graph 708 represents a concentration of oxygen consumed by an evaporated non-aromatic hydrocarbon at the oxygen sensor.

Prior to T1, an engine oil is changed (e.g., renewed) and an engine start is initiated. The engine oil temperature upon engine start is below a threshold engine oil temperature (e.g., 80° C.), also known as an engine cold start. During the engine cold start, liquid fuel (e.g., hydrocarbons) impinges on a cylinder bore wall due to a lower intake air charge temperature and reduced rate of evaporation of a fuel spray. The fuel impinging on the walls can accumulate inside the crankcase oil pan at a rate that depends on an engine cooling capacity (e.g., a greater engine cooling capacity may result in a longer oil warm-up time and therefore greater fuel in the crankcase), vehicle driving cycles (e.g., shorter driving cycles may result in an engine oil remaining below the threshold engine temperature), and climate conditions (e.g., colder climates may delay engine temperatures increasing). Aromatic and non-aromatic hydrocarbons begin to accumulate in the engine oil in the crankcase, as seen by graphs 704 and 702 respectively. The aromatic hydrocarbons increase to approximately 1% weight fuel in oil and the non-aromatic hydrocarbons increase to approximately 0.2% weight fuel in oil. The aromatic hydrocarbons and non-aromatic hydrocarbons do not evaporate out of the crankcase and do not consume oxygen, as seen by graphs 706 and 708 respectively.

At T1, the aromatic and non-aromatic hydrocarbons begin to evaporate out of the oil sump and consume the oxygen at an oxygen sensor, such as a sensor in an intake manifold (e.g., hydrocarbons are oxidized by the oxygen) due to the engine oil beginning to warm up. The aromatic and non-aromatic hydrocarbons continue to accumulate in the engine oil of the crankcase.

After T1 and prior to T2, the engine is operated under a variety of conditions attempting to replicate multiple engine cold-starts. In one example, the engine is operated through five FTP 505 drive cycles in a wind tunnel with 0° F. conditions for approximately 10 minutes. In another example, the engine may be subject to multiple cold starts with light load operation during the time between T1 and T2. As a result, the aromatic and non-aromatic hydrocarbons increase, due to the cold-starts, at a fairly similar rates due to the engine oil temperature still being less than the threshold temperature to approximately 2.5% and 2% weight fuel in oil, respectively. The aromatic hydrocarbons and non-aromatic hydrocarbons consumption of oxygen increases to approximately 0.02% and 0.1% respectively.

The intake air oxygen sensor measures a concentration of oxygen in an intake air via a catalyst within the sensor reacting with oxygen. When hydrocarbons evaporate from the oil in the crankcase, the hydrocarbons may react with the oxygen on the sensor catalyst before the sensor measures the concentration of oxygen (e.g., oxygen oxidizes the hydrocarbon to carbon dioxide). This process alters an oxygen sensor reading to measurement to measure a concentration of oxygen less than an actual concentration of oxygen in the intake air. As a result, a controller may receive this measurement and decrease an EGR rate in order to maintain desired stoichiometric conditions in a combustion chamber.

As described above with respect to FIG. 6, the impact of the hydrocarbon may be learned and applied to At T2, the aromatic and non-aromatic hydrocarbons continue to consume oxygen in the intake manifold. The aromatic and non-aromatic hydrocarbons continue to accumulate in the engine oil in the crankcase.

After T2 and prior to T3, the engine is again exposed to a variety of conditions attempting to replicate multiple engine cold-starts. In one example, the engine may be operated to simulate multiple cold-starts substantially equivalent to two weeks of driving short, lightly-loaded driving cycles in colder climates. The concentration of the aromatic and non-aromatic hydrocarbons both continue to increase to approximately 6% weight fuel in oil. The concentration of the two types of hydrocarbons become substantially equal. Additionally, the aromatic and non-aromatic hydrocarbons consume an increased concentration of oxygen (approximately 0.1% and 0.2%, respectively) in the intake manifold.

As depicted, the effect of the non-aromatic hydrocarbons is greater than the effect of aromatic hydrocarbons on the intake air oxygen sensor (e.g., more oxygen is consumed) because there is a higher molar concentration of non-aromatic hydrocarbons than aromatic hydrocarbons in the engine oil. According to equation 7, a higher molar concentration results in a higher partial pressure which may result in an increased effect on the intake air oxygen sensor.

At T3, the concentration of the aromatic and non-aromatic hydrocarbons in the engine oil begins to decrease. This may be due to the engine oil reaching the threshold engine oil temperature (e.g., 80° C.). By reaching the threshold engine oil temperature, the likelihood of the hydrocarbons impinging on the combustion chamber walls decreases and hydrocarbons may no longer accumulate in the crankcase oil sump. Furthermore, light-chain hydrocarbons may no longer be present in the engine oil and may not affect the intake air oxygen sensor. The aromatic and non-aromatic hydrocarbons continue to consume oxygen in the intake manifold.

After T3 and prior to T4, the engine is operated with parameters aimed at evaporating fuel from the oil in the crankcase. As one example, the engine operation includes driving at 55 m.p.h. with an open active grill shutter. Engine oil was kept at approximately 80° C. As a result, the concentration of the aromatic and non-aromatic hydrocarbons in the engine oil decreases to approximately 3% and 4% weight fuel in oil, respectively. The concentration of oxygen consumed by the aromatic and non-aromatic hydrocarbons increases to approximately 0.15% and 0.25% respectively.

At T4, the concentration of the aromatic and non-aromatic hydrocarbons in the engine oil continues to decrease as the hydrocarbons evaporate out of the crankcase during purge. The evaporated aromatic and non-aromatic hydrocarbons continue to consume the oxygen at the oxygen sensor at an increased amount.

After T4 and prior to T5, the engine operation still aims at evaporation fuel from the oil in the crankcase. As one example, the engine operation includes driving at 55 m.p.h with a closed active grill shutter. Engine oil was kept at approximately 96° C. As a result, the vapor pressure of the hydrocarbons increases and the concentration of the aromatic and non-aromatic hydrocarbons in the engine oil continues to decrease. The amount of oxygen consumed by the aromatic and non-aromatic hydrocarbon increases. The percentage sum of the amount of oxygen consumed increases to approximately 0.4%.

At T5, the concentration of the aromatic and non-aromatic hydrocarbons in the engine oil continues to decrease as the hydrocarbons evaporate out of the crankcase during purge. The evaporated aromatic and non-aromatic hydrocarbons consume the oxygen at the oxygen sensor at a decreased rate. This may be due to the concentration of the hydrocarbons in the engine oil substantially decreasing (e.g., molar concentration decreases), and thereby the vapor pressure of the hydrocarbons decreases causing a decreased consumption of oxygen. Additionally or alternatively, as the percent weight fuel in oil decreases to a value of zero, hydrocarbons may no longer be present in the engine oil and effect the intake air oxygen sensor.

FIG. 8 depicts method 800 for using an IAO2 sensor to determine a HC presence in a crankcase oil.

Method 800 begins at 802, in which the method 800 includes determining, estimating, and/or measuring current engine operating parameters. The engine operating parameters include but are not limited to a charge air demand, throttle position, mass air pressure, air intake temperature, engine speed, engine temperature, engine load, intake oxygen content, and an air/fuel ratio.

At 804, the method 800 includes determining if EGR is activated. If EGR is flowing then the method 800 proceeds to 806 to maintain current engine operating parameters and not use the IAO2 sensor as an onboard HC sensor. The method may exit. In some embodiments, additionally or alternatively, if EGR is activated, the method 800 may include adjusting the EGR flow rate based on a determined hydrocarbon effect on the IAO2 sensor. As described above, the determined hydrocarbon effect may be based on a current engine operation. In one example, a predicted effect on the IAO2 may be obtained from a look up table generated as described above that maps IAO2 effect to engine load, speed, temperature, etc. In some examples, the predicated IAO2 sensor effect may be based on a previous crankcase hydrocarbon concentration determination, where the IAO2 measures hydrocarbons present in the PCV purge vapors, as described in more detail below.

If the EGR is disabled, then the method 800 proceeds to 808 to determine if canister purge is activated. As described above with respect to FIG. 2, a vehicle fuel tank may emit gasoline fumes to a canister, which then purges the excess fumes to the engine. If canister purge is active, the method 800 may proceed to 806, as described above, and not allow the canister purge to potentially falsify onboard IAO2 HC measurements. The method may exit.

If canister purge is disabled, the method 800 proceeds to 810 to use the IAO2 sensor as an onboard HC sensor during PCV purge. The IAO2 sensor measures an oxygen content of an engine intake. The method 800 proceeds to 812 to determine if hydrocarbons are present in the crankcase oil by measuring if a difference exists between the oxygen content measured prior to the PCV purge (which may include the oxygen content measured at 802 or known ambient oxygen concentration) and the oxygen content measured at 810. If the oxygen content at 810 is substantially equal to the oxygen content measured at 802, then it is determined no hydrocarbons are present in the crankcase and the method proceeds to 806 to maintain current engine operating parameters.

If a difference exists between the oxygen contents measured at 802 and 810, such as if the oxygen content measured after PCV purge begins is less than the oxygen content prior to PCV purge, then hydrocarbons are present in the oil in the crankcase and the method 800 proceeds to 814 At 814 the method includes activating an indicator lamp to alert a consumer of a demanded engine maintenance (e.g., the high levels of hydrocarbons may indicate excessive fuel in the oil or engine degradation). In some examples, the indicator lamp may be activated only if the measured oxygen content during PCV purge is less than intake air oxygen content prior to PCV purge by more than a threshold amount. In this way, the effect of a hydrocarbon in an engine oil of a crankcase oil sump on an intake air oxygen sensor may be measured and estimated for individual hydrocarbons. Additionally, the effects of both aromatic and non-aromatic hydrocarbons may be measured and totaled to determine an effect on an oxygen sensor. By doing this, a cylinder air/fuel ratio may be met while also decreasing emissions. The technical effect of characterizing individual hydrocarbons is to determine an accurate effect of the hydrocarbon on the oxygen sensor. Hydrocarbons behave differently from one another and their oxidation in the presence of oxygen and heat is not necessarily equal from one hydrocarbon to a second, different hydrocarbon. Therefore, it may be preferred to identify an individual hydrocarbon and estimate its impact on the intake air oxygen sensor upon evaporation.

An apparatus comprising an analyzer to analyze an engine fluid and a computing device operably coupled to the analyzer, the computing device storing non-transitory instructions executable to determine fuel dilution in engine oil based on speciation of hydrocarbons in fuel in the engine oil determined based on output received from the analyzer. The engine fluid is the engine oil, the engine oil sampled from an engine oil sump of an engine, and where the analyzer comprises a gas chromatographer configured to output one or more retention times of the engine oil. The analyzer further comprises a mass spectrometer to detect output from the gas chromatographer. The gas chromatographer outputs a plurality of retention times each corresponding to a fraction of the engine oil, and wherein the instructions are executable to identify at least one hydrocarbon species present in each fraction based at least on a corresponding retention time. Additionally or alternatively, the instructions are further executable to identify or more of a molecular weight of that fraction, boiling point of that fraction, and vapor pressure of each identified hydrocarbon species in the engine oil. The instructions are further executable to identify one or more of a molar concentration, partial pressure, and molar fraction of each identified hydrocarbon species in the engine oil.

The apparatus, additionally or alternatively, further includes the instructions are further executable to identify one or more of a molar concentration, partial pressure, and molar fraction of each identified hydrocarbon species in a gaseous phase of an engine compartment housing the oil sump. The instructions are further executable to identify a predicted effect on an oxygen sensor based on the retention time and molar fraction of each identified hydrocarbon species in the gaseous phase. The instructions are further executable to output the predicted effect for display on a display device. The instructions, additionally or alternatively, are executable to receive an oxygen concentration measured by the oxygen sensor, the oxygen sensor positioned to sample intake air or exhaust gas of the engine, determine a difference between the measured oxygen concentration and an expected oxygen concentration, and if the difference is greater than a threshold, adjust a calibration value of the oxygen sensor, the expected oxygen concentration based on the predicted effect on the oxygen sensor. The instructions are further executable to output an identity and/or concentration of the identified one or more hydrocarbon species within the engine oil for display on a display device.

An engine testing apparatus, comprising a gas chromatographer mass spectrometer (GC-MS) configured to sample an engine fluid and determine, for each of a plurality of fractions of the engine fluid, a retention time, and a computing device operably coupled to the GC-MS, the computing device storing non-transitory instructions executable to identify one or more hydrocarbon species present in the engine fluid based on each retention time. The engine fluid is engine oil. The instructions of the engine testing apparatus, additionally or alternatively, are further executable to determine a concentration of each identified hydrocarbon species present in the engine fluid based on each retention time and corresponding mass spectrometer ion count. The instructions of the engine testing apparatus, additionally or alternatively, are further executable to output a notification of an identity and concentration of each identified hydrocarbon species present in the engine fluid for display on a display device. The instructions are further executable to determine a predicted effect on an oxygen sensor based on each retention time and output a notification of the predicted effect for display on a display device.

A second engine testing apparatus, comprising a gas chromatographer mass spectrometer (GC-MS) configured to sample engine oil and determine, for each of a plurality of fractions of the engine oil, a retention time, and a computing device operably coupled to the GC-MS, the computing device storing non-transitory instructions executable to identify one or more hydrocarbon species and a concentration of each identified hydrocarbon species present in the engine oil based on each retention time and determine a predicted effect on an oxygen sensor based on each retention time. The engine oil is sampled from an oil sump positioned in a crankcase of an engine, and wherein the oxygen sensor is positioned to sample intake air or exhaust gas of the engine. The instructions are executable to output a notification of the predicted effect on the oxygen sensor for display on a display device. The identifying includes identifying one or more of a molecular weight, vapor pressure, boiling point, and a type of hydrocarbon for one or more hydrocarbon species.

Note that the example control and estimation routines included herein can be used with various engine and/or vehicle system configurations. The control methods and routines disclosed herein may be stored as executable instructions in non-transitory memory and may be carried out by the control system including the controller in combination with the various sensors, actuators, and other engine hardware. The specific routines described herein may represent one or more of any number of processing strategies such as event-driven, interrupt-driven, multi-tasking, multi-threading, and the like. As such, various actions, operations, and/or functions illustrated may be performed in the sequence illustrated, in parallel, or in some cases omitted. Likewise, the order of processing is not necessarily required to achieve the features and advantages of the example embodiments described herein, but is provided for ease of illustration and description. One or more of the illustrated actions, operations and/or functions may be repeatedly performed depending on the particular strategy being used. Further, the described actions, operations and/or functions may graphically represent code to be programmed into non-transitory memory of the computer readable storage medium in the engine control system, where the described actions are carried out by executing the instructions in a system including the various engine hardware components in combination with the electronic controller.

It will be appreciated that the configurations and routines disclosed herein are exemplary in nature, and that these specific embodiments are not to be considered in a limiting sense, because numerous variations are possible. For example, the above technology can be applied to V-6, I-4, I-6, V-12, opposed 4, and other engine types. The subject matter of the present disclosure includes all novel and non-obvious combinations and sub-combinations of the various systems and configurations, and other features, functions, and/or properties disclosed herein.

The following claims particularly point out certain combinations and sub-combinations regarded as novel and non-obvious. These claims may refer to "an" element or "a first" element or the equivalent thereof. Such claims should be understood to include incorporation of one or more such elements, neither requiring nor excluding two or more such elements. Other combinations and sub-combinations of the disclosed features, functions, elements, and/or properties may be claimed through amendment of the present claims or through presentation of new claims in this or a related application. Such claims, whether broader, narrower, equal, or different in scope to the original claims, also are regarded as included within the subject matter of the present disclosure.

The invention claimed is:

1. An apparatus, comprising:
    an analyzer including a port to receive engine oil from an engine that has undergone fuel combustion, thereby subjecting the engine oil to fuel products, the analyzer configured to measure molecular parameters of each fraction of the engine oil and output the measured molecular parameters; and
    a computing device operably coupled to the analyzer, the computing device storing non-transitory instructions executable to:
        receive the measured molecular parameters output from the analyzer;
        identify one or more individual hydrocarbon species in the fuel products in the engine oil based on the measured molecular parameters received from the analyzer and a model derived from analyzer data collected from a set of known hydrocarbon species; and
        output a notification of the identified one or more individual hydrocarbon species for display on a display device.

2. The apparatus of claim 1, wherein the engine oil is sampled from an engine oil sump of the engine, and where the analyzer comprises a gas chromatographer configured to output the measured molecular parameters, the measured molecular parameters including one or more retention times of the engine oil.

3. The apparatus of claim 2, wherein the analyzer further comprises a mass spectrometer to detect output from the gas chromatographer.

4. The apparatus of claim 3, wherein the gas chromatographer outputs a plurality of retention times each corresponding to a fraction of the engine oil, and wherein the instructions are executable to identify at least one hydrocarbon species present in each fraction based at least on a corresponding retention time.

5. The apparatus of claim 4, wherein the instructions are further executable to identify one or more of a molecular weight of that fraction, a boiling point of that fraction, and a vapor pressure of each identified hydrocarbon species in the engine oil.

6. The apparatus of claim 4, wherein the instructions are further executable to identify one or more of a molar concentration, apartial pressure, and a molar fraction of each identified hydrocarbon species in the engine oil.

7. The apparatus of claim 4, wherein the instructions are further executable to identify a molar fraction of each identified hydrocarbon species in a gaseous phase of an engine compartment housing the engine oil sump.

8. The apparatus of claim 7, wherein the instructions are further executable to identify a predicted effect on an oxygen sensor based on the retention time and molar fraction of each identified hydrocarbon species in the gaseous phase.

9. The apparatus of claim 8, wherein the instructions are further executable to output the predicted effect for display on the display device.

10. The apparatus of claim 8, wherein the instructions are executable to:
    receive an oxygen concentration measured by the oxygen sensor, the oxygen sensor positioned to sample intake air or exhaust gas of the engine,
    determine a difference between the measured oxygen concentration and an expected oxygen concentration determined based on the predicted effect on the oxygen sensor, and
    if the difference is greater than a threshold, adjust a calibration value of the oxygen sensor.

11. The apparatus of claim 2, wherein the instructions are further executable to output a concentration of the identified one or more hydrocarbon species for display on the display device.

12. An engine testing apparatus, comprising:
    a gas chromatographer mass spectrometer (GC-MS) configured to sample an engine fluid and measure a respective retention time for each of a plurality of fractions of the engine fluid; and
    a computing device operably coupled to the GC-MS, the computing device storing non-transitory instructions executable to:
        identify one or more hydrocarbon species present in the engine fluid based on each retention time and a model derived from GC-MS data collected from a set of known hydrocarbon species; and
        output a notification of the identified one or more hydrocarbon species for display on a display device.

13. The engine testing apparatus of claim 12, wherein the engine fluid is engine oil sampled from an oil sump of an engine that has undergone fuel combustion, thereby providing fuel products to the engine oil, and wherein the identified one or more hydrocarbon species present in the engine oil comprise or are derived from the fuel products.

14. The engine testing apparatus of claim 12, wherein the GC-MS is configured to measure a respective mass spectrometer ion count for each of the plurality of fractions of the engine fluid, and wherein the instructions are further executable to determine a concentration of each identified hydrocarbon species present in the engine fluid based on each retention time and corresponding mass spectrometer ion count.

15. The engine testing apparatus of claim 14, wherein the instructions are further executable to output a notification of an identity and concentration of each identified hydrocarbon species present in the engine fluid for display on the display device.

16. The engine testing apparatus of claim 12, wherein the instructions are further executable to determine a predicted effect on an oxygen sensor based on each retention time and output a notification of the predicted effect for display on the display device.

17. An engine testing apparatus, comprising:
- a gas chromatographer mass spectrometer (GC-MS) configured to sample engine oil and determine, for each of a plurality of fractions of the engine oil, a retention time; and
- a computing device operably coupled to the GC-MS, the computing device storing non-transitory instructions executable to:
  - identify one or more hydrocarbon species and a concentration of each identified hydrocarbon species present in the engine oil based on each retention time and a model derived from GC-MS data collected from a set of known hydrocarbon species;
  - determine a calibration value usable for calibrating an oxygen sensor of a vehicle based on each retention time; and
  - output a notification of the calibration value for display on a display device.

18. The engine testing apparatus of claim 17, wherein the engine oil is sampled from an oil sump positioned in a crankcase of an engine of the vehicle, and wherein the oxygen sensor is positioned to sample intake air or exhaust gas of the engine.

19. The engine testing apparatus of claim 17, wherein the identifying includes identifying one or more of a molecular weight, a vapor pressure, a boiling point, and a type of hydrocarbon for the one or more hydrocarbon species.

* * * * *